(12) United States Patent  
Chakravarthy et al.

(10) Patent No.: US 10,722,133 B2  
(45) Date of Patent: Jul. 28, 2020

(54) QT INTERVAL DETERMINATION METHODS AND RELATED DEVICES

(71) Applicant: Medtronic Monitoring, Inc., San Jose, CA (US)

(72) Inventors: Niranjan Chakravarthy, Eden Prairie, MN (US); Abhi Chavan, Gaithersburg, MD (US); Scott Williams, Minneapolis, MN (US); Rao Gudivada, Chao Chu Kang (SG)

(73) Assignee: MEDTRONIC MONITORING, INC., San Jose, CA (US)

( * ) Notice: Subject to any disclaimer, the term of this patent is extended or adjusted under 35 U.S.C. 154(b) by 30 days.

(21) Appl. No.: 15/975,099

(22) Filed: May 9, 2018

(65) Prior Publication Data

US 2018/0256060 A1 Sep. 13, 2018

Related U.S. Application Data

(63) Continuation of application No. 14/543,180, filed on Nov. 17, 2014, now Pat. No. 9,986,932.

(51) Int. Cl.
| | |
|---|---|
| *A61B 5/05* | (2006.01) |
| *A61B 5/0472* | (2006.01) |

(Continued)

(52) U.S. Cl.
CPC .......... *A61B 5/0472* (2013.01); *A61B 5/0006* (2013.01); *A61B 5/0245* (2013.01);

(Continued)

(58) Field of Classification Search
CPC .............................. A61B 5/0452; A61B 5/0472
See application file for complete search history.

(56) References Cited

U.S. PATENT DOCUMENTS

| 4,531,527 A | 6/1985 | Reinhold, Jr. et al. |
| 5,027,824 A | 7/1991 | Dougherty et al. |

(Continued)

FOREIGN PATENT DOCUMENTS

| AU | 2013267073 A1 | 1/2014 |
| CA | 2540756 A1 | 10/2001 |

(Continued)

OTHER PUBLICATIONS

International Search Report and Written Opinion dated Apr. 1, 2016 for PCT Application No. PCT/US2015/059948.

(Continued)

*Primary Examiner* — Michael J D Abreu  
(74) *Attorney, Agent, or Firm* — Shumaker & Sieffert, P.A.

(57) ABSTRACT

Described herein is a system and method of automatically monitoring QT intervals in a patient based on one or more EKG signals received from attached monitoring devices. Each EKG signal is analyzed to detect attributes of the first and second EKG signals, including QRS onset information, QRS peak information, and T-wave offset information. A QT interval is calculated based on QRS onset information derived from the first EKG signal and T-wave offset information derived from the second EKG signal. The calculated QT interval is compared to thresholds to detect elongation of the QT interval and an alert is generated in response to a detected elongated QT interval.

20 Claims, 13 Drawing Sheets

(51) Int. Cl.
*A61B 5/00* (2006.01)
*A61B 5/04* (2006.01)
*A61B 5/0245* (2006.01)
*A61B 5/0452* (2006.01)
*G16H 50/30* (2018.01)

(52) U.S. Cl.
CPC ........ *A61B 5/04012* (2013.01); *A61B 5/0452* (2013.01); *A61B 5/6823* (2013.01); *A61B 5/7275* (2013.01); *A61B 5/7285* (2013.01); *G16H 50/30* (2018.01)

(56) References Cited

U.S. PATENT DOCUMENTS

| | | | |
|---|---|---|---|
| 8,326,407 B2 | 12/2012 | Linker | |
| 8,433,395 B1* | 4/2013 | Brockway | A61B 5/7203 600/509 |
| 8,798,727 B2 | 8/2014 | Linker | |
| 8,897,863 B2 | 11/2014 | Linker | |
| 2004/0077941 A1 | 4/2004 | Reddy et al. | |
| 2009/0062671 A1 | 3/2009 | Brockway | |
| 2009/0076345 A1 | 3/2009 | Manicka et al. | |
| 2009/0318822 A1 | 12/2009 | Qu et al. | |
| 2010/0204599 A1* | 8/2010 | Pu | A61B 5/0402 600/523 |
| 2013/0131530 A1 | 5/2013 | Brockway et al. | |

FOREIGN PATENT DOCUMENTS

| | | |
|---|---|---|
| CN | 1163741 A | 11/1997 |
| CN | 102389303 A | 3/2012 |
| WO | 9211807 A1 | 7/1992 |

OTHER PUBLICATIONS

"Drug-induced QT prolongation", Wikipedia, https://en.wikipedia.org/wiki/Drug-induced_QT_prolongation, last viewed Jan. 12, 2017.
"E14 Clinical Evaluation of QT/QTc Interval Prolongation and Proarrhythmic Potential for Non-Antiarrhythmic Drugs", Guidance for Industry, Oct. 2005, http://www.fda.gov/downloads/Drugs/GuidanceComplianceRegulatoryInformation/Guidances/ucm073153.pdf.
"Long Qt syndrome", Wikipedia, https://en.wikipedia.org/wiki/Long_QT_syndrome, last viewed Jan. 11, 2017.
"Needleman—Wunsch algorithm", Wikipedia, http://en.wikipedia.org/wiki/Needleman%E2%80%93Wunsch_algorithm, last viewed Jan. 11, 2017.
"QTc Prolongation and Risk of Sudden Cardiac Death: Is the Debate Over?", Medscape, http://www.medscape.com/viewarticle/522879, Feb. 3, 2006.
Badilini, "The 'Thorough QT study': A valid paradigm to test new algorithms for QT interval measurements?", Journal of Electrocardiology 46 (2013): 126-127.
Fogoros, "Long QT Syndrome A Common Cause of Sudden Death in Young People", https://www.verywell.com/long-qt-syndrome-1745221, Updated Jul. 27, 2016.
Goldenberg, et al., "QT Interval: how to Measure It and What is "Normal"", Journal of Cardiovascular Electrophysiology, vol. 17, No. 3, Mar. 1, 2006.
Haghpanah, et al., "Scoring Consensus of Multiple ECG Annotators by Optimal Sequence Alignment", IEE EMBS, Aug. 2014,, 1855-1859.
Helfenbein, et al., "An algorithm for continuous real-time QT interval monitoring", Journal of Electrocardiology, Elsevier Science, XX, vol. 39, No. 4, Oct. 1, 2006, S123-S127.
Karjalainen, et al., "Relation Between QT Intervals and Heart Rates From 40 to 120 beats/min in Rest Electrocardiograms of Men and a Simple Method to Adjust QT Interval Values", JACC, vol. 23, No. 7, Jun. 1994, 1547-53.
Schwartz, et al., "Diagnostic Criteria for the Long QT Syndrome an Update", Circulation, vol. 88, No. 2, Aug. 1993.
Notification of Grant, and translation thereof, from counterpart Chinese Application No. 2015800735354, dated Dec. 26, 2019, 14 pp.
Prosecution History from U.S. Appl. No. 14/543,180, dated Jul. 26, 2016 through Feb. 16, 2018, 87 pp.
International Preliminary Report on Patentability from International Application No. PCT/US2015/059948, dated May 23, 2017, 11 pp.

* cited by examiner

QT INTERVAL DETERMINATION METHODS AND RELATED DEVICES

TECHNICAL FIELD

The present disclosure relates to monitoring devices and methods, and in particularly to devices and methods for determining and monitoring QT intervals in patients.

BACKGROUND

Monitoring of the heart's electrical signals—electrocardiogram signals—is utilized to monitor the cardiac cycle of patients in order to detect various conditions and disorders. A typical cardiac cycle as represented by an electrocardiogram signal (EKG) consists of a P wave, a QRS complex, and a T wave—which appear in that order. An EKG specialist is trained to analyze aspects of the EKG signal to identify potential disorders or dangers. The P-wave represents the electrical signal created during atrial depolarization; the QRS complex reflects the rapid depolarization of the right and left ventricles following the atrial depolarization (P-wave); and the T-wave represents the repolarization or recovery of the ventricles. The ventricles are larger muscles than the atria, and therefore the depolarization associated with the QRS complex is typically greater in magnitude than the P-wave depolarization or T-wave repolarization. Analysis of the EKG signal includes measurements related to the timing and magnitude of the components of the EKG signal. For example, heart rate is detected based on the interval between successive peaks of the R portion of the QRS complex (e.g., the R-R interval). The PR interval is measured from the beginning of the P wave to the beginning of the QRS complex and reflects the time the electrical impulse takes to travel from the sinus node through the AV node, and provides an indication of AV node function. Likewise, the QT interval is measured form the beginning of the QRS complex to the end of the T wave. With respect to the measured QT interval, a prolonged QT interval has been identified as a risk factor for a number of conditions, such as acute myocardial infarction and ischemia, hypocalcemia, central nervous system events, hypothermia, hypothyroidism, and as a result of medication.

In a hospital setting, a 6-lead configuration or 12-lead configuration is typically utilized to collect EKG signals and measure the QT interval. However, this type of cardiac monitoring typically only takes place in a hospital for a limited period of time, and typically while the patient is non-ambulatory. It would be desirable to provide long-term monitoring (e.g., multiple days) of cardiac activity—and QT interval detection in particular—in order to detect extreme QT interval events that occur infrequently and/or enable the detection of gradual changes in QT interval. In addition, it would be desirable to monitor a patient's QT interval while the patient is active or engaged in activities such as standing up or walking around. Finally, it would be beneficial to be able to monitor and detect a patient's QT interval without the full complement of six or twelve leads typically used for EKG monitoring in a hospital.

SUMMARY

According to one example of the disclosure, a monitoring system that measures QT intervals in patients includes a first monitoring device and a QT interval measurement module. The first monitoring device is adhered to a patient at a first location and monitors a first electrocardiogram (EKG) signal associated with the patient. The QT interval measurement module is configured to receive the first EKG signal from the first monitoring device, and is configured to identify QRS complex attributes and heart rate attributes for each beat within the received first EKG signal. Based on identified QRS complex information, the QT interval measurement module locates heart rate attributes a T-wave offset (iToff) for each beat. The QT interval measurement module further selects qualified beat segments comprised of a plurality of beats suitable for QT interval measurement within the received first EKG signal, and measures QT intervals within the qualified beat segments based on QRS complex attributes and T-wave offsets identified with respect to each beat.

According to another example of the disclosure, a monitoring system that measures QT intervals in patients includes first and second monitoring devices, and a QT interval measurement module. The first monitoring device is adhered to a patient at a first location and monitors a first electrocardiogram (EKG) signal associated with the patient. The second monitoring device is adhered to a patient at a second location different than the first location and monitors a second EKG signal associated with the patient. The QT interval measurement module is configured to receive the first and second EKG signals from the first and second monitoring devices, respectively, and identify first attributes associated with the first EKG signal and second attributes associated with the second EKG signal. The QT interval measurement module selects qualified beat segments comprised of a plurality of beats suitable for QT interval measurement within the received first and second EKG signals, and measures QT intervals within the qualified beat segments based on a combination of the first attributes associated with the first EKG signal and second attributes associated with the second EKG signal.

According to another embodiment of the disclosure, a method of automatically monitoring QT intervals in a patient includes receiving global timing information at a first adherent device and a second adherent device. The first adherent device measures a first electrocardiogram (EKG) signal and associates a timestamp with the first EKG signal based on received global timing information. The second adherent device measures a second EKG signal and associates a timestamp with the second EKG signal based on received global timing information. The first and second measured EKG signals and timestamp information is communicated from the respective adherent devices to a processor system. A QT interval is calculated based on the first and second EKG signals, wherein the QT interval is calculated based on QRS onset information derived from the first EKG signal and T-wave offset information derived from the second EKG signal. The calculated QT interval is compared to thresholds to detect elongation of the QT interval and an alert is generated in response to a detected elongated QT interval.

According to another embodiment of the disclosure, a method of detecting QT intervals includes receiving a first electrocardiogram (EKG) signal from a first device located in a first lead configuration on a patient's abdomen and receiving a second EKG signal from a second device located in a second lead configuration located on the patient's chest at a defined angle relative to the first device. QRS onset and QRS peak information are detected with respect to the first EKG signal and QRS peak and T-wave offset information with respect to the second EKG signal. A first plurality of beats associated with the first measured EKG signal are matched with a second plurality of beats associated with the second EKG signal to align the QRS peaks of the first plurality of beats with the QRS peaks of the second plurality of beats. A QT interval is calculated based on the detected QRS onset information associated with the first EKG signal and T-wave offset information associated with the second EKG signal. Abnormalities in the QT interval are detected based on the calculated QT interval.

DETAILED DESCRIPTION

The present invention provides a system and method of measuring the QT interval and automatically detecting conditions related to the QT interval such as Long QT Syndrome (LQTS). In one embodiment, a first EKG signal generated from a first lead configuration (e.g., first location/orientation of an electrocardiogram device) is utilized to gather some information related to some aspects of the cardiac cycle (e.g., QRS onset) and a second EKG signal generated from a second lead configuration (e.g., second location/orientation of an electrocardiogram device) is utilized to gather additional information related to aspects of the cardiac cycle (e.g., P-wave offset). The first and second EKG signals are synchronized with one another such that the QT interval may be measured based on QRS onset information obtained from one EKG signal and T-wave offset information obtained from the other EKG signal. The calculated QT interval is then analyzed to detect conditions associated with QT interval elongation, including both intermittent events and gradual changes to the QT interval.

Figure 1:
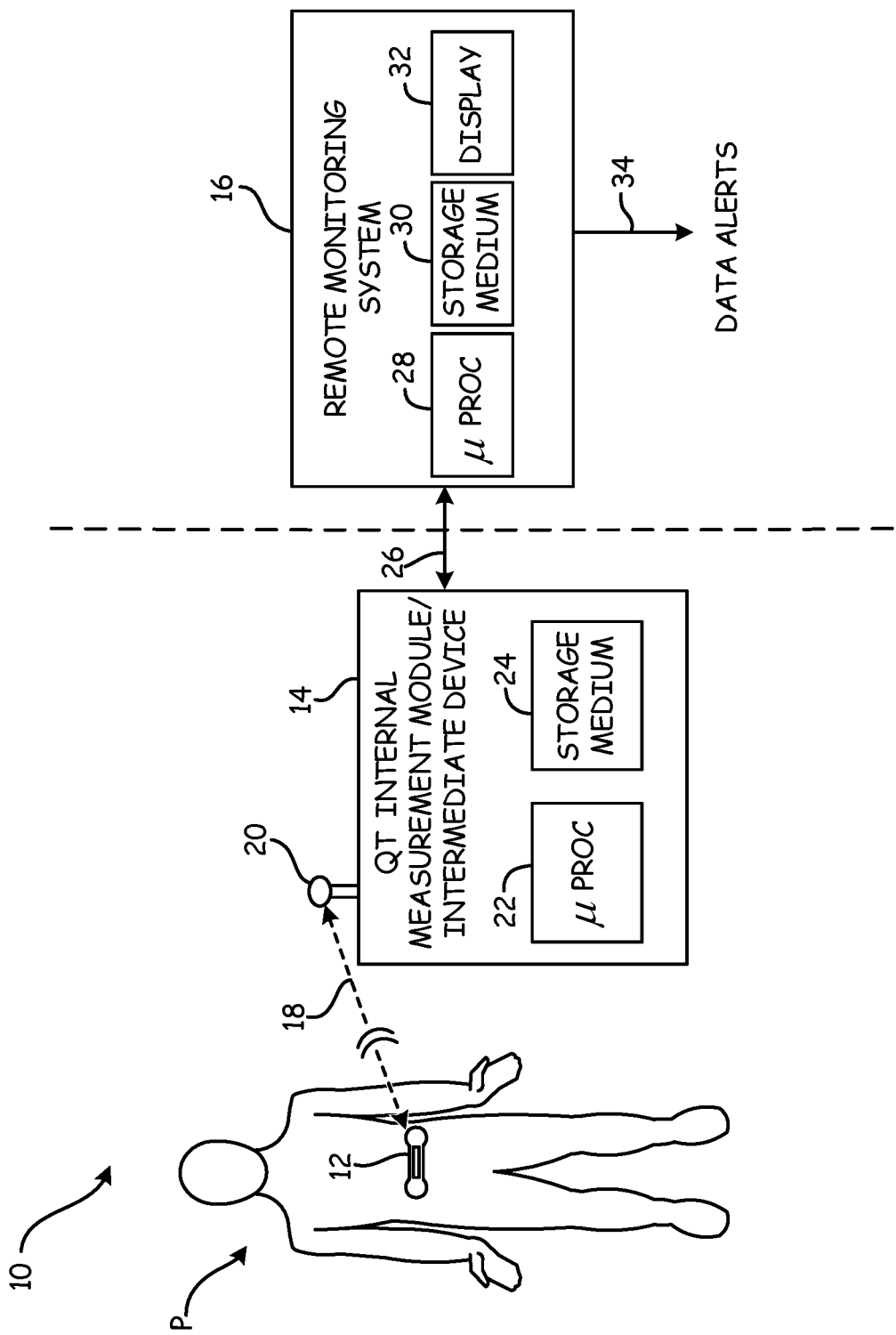
FIG. 1 illustrates a schematic view of a monitoring and treatment system that measures electrocardiogram signals and performs analysis to measure QT intervals according to an embodiment of the present invention.

FIG. 1 illustrates a schematic view of monitoring and treatment system 10 that measures electrocardiogram signals and performs analysis to measure QT intervals according to an embodiment of the present invention. In the embodiment shown in FIG. 1, monitoring and treatment system 10 includes monitoring device 12, intermediate/QT interval measurement module 14, and remote monitoring system 16. Intermediate/QT interval measurement module 14 includes antenna 20, micro-processor 22, and storage medium 24. In one embodiment, intermediate device 14 is responsible for processing EKG signals received from monitoring device 12 to measure the QT interval associated with the patient, and report/alert detected problems to medical personnel at remote monitoring system 16. However, in other embodiments, intermediate device 14 is simply an intermediary between monitoring device 12 and remote monitoring system 16, wherein processing of the EKG signals is performed either locally at monitoring device 12 or remotely at remote monitoring system 16. Remote monitoring system 16 includes micro-processor 28, storage medium 30, and display 32.

Figure 10A:
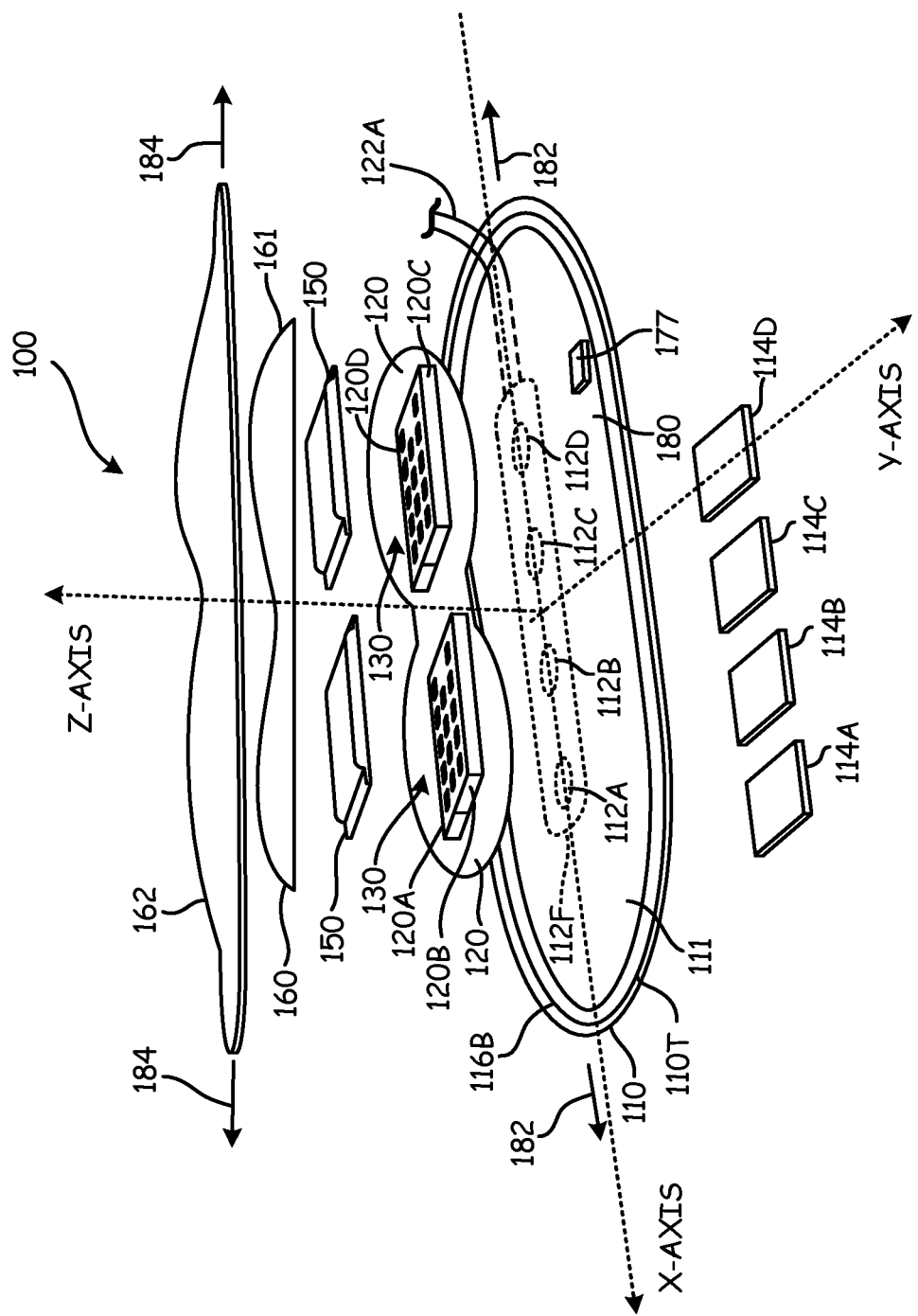
FIGS. 10A and 10B show an exploded view and a side cross-sectional view, respectively, of adherent devices utilized to measure EKG signals according to embodiments of the present invention.
Figure 10B:
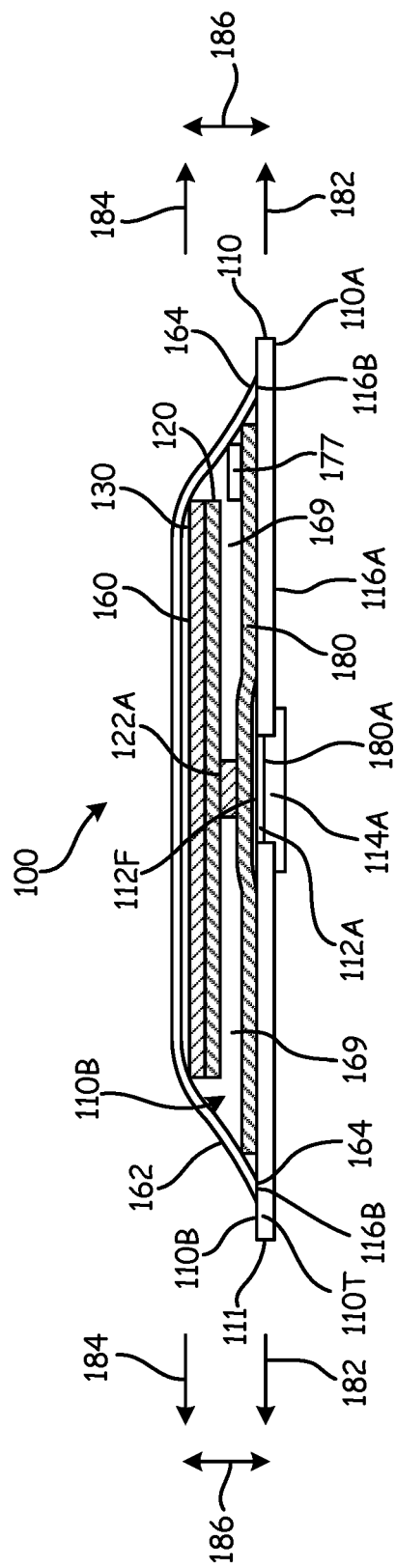

Monitoring device 12 is adhered, attached, or otherwise placed in a position to monitor electrocardiogram signals in patient P. An embodiment of one such monitoring device is shown in FIGS. 10a-10b. In some embodiment, monitoring device 12 includes a local processor (not shown) capable of analyzing sensed EKG signal, while in other embodiments monitoring device 12 maintains a local processor/controller capable only of communicating measured EKG signals to intermediate device 14 or remote monitoring system 16 for further processing and/or analysis.

In one embodiment, first and second EKG signals are utilized in conjunction with one another to measure the QT interval. The first EKG signal is measured by monitoring device 12 at a first location—such as that shown in FIG. 1—and the second EKG signal is measured by monitoring device 12 at a second location. For example, in one embodiment the first location is located on patient P's abdomen at an angle approximately parallel with the horizon, and the second location is located on patient P's chest at an angle of approximately forty-five degrees to the horizon—as well as forty-five degrees to the orientation of the device at the first location. In one embodiment, this requires first and second monitoring devices adhered or otherwise connected to patient P. In other embodiments however, the same device may be utilized at different instances in time to capture EKG data from the desired first and second lead positions.

Communication and processing of EKG signal(s) sensed with respect to patient P will be performed by the QT interval measurement module, but this module can reside in any device that has access to the measured EKG signals and has a processor/storage medium for enabling processing of the EKG signals. For example, in the embodiment shown in FIG. 1 QT interval measurement module may be implemented locally at monitoring device 12, at intermediate device 14 (as shown in FIG. 1), and/or at remote monitoring system 16. Depending on the application, it may be beneficial to perform EKG processing locally on processors included as part of monitoring device 12 and communicate to intermediate device 14 and/or remote monitoring system 16 only the processed results (e.g., measured QT intervals, etc.). In other applications, it may be beneficial to perform processing of the EKG signal(s) at intermediate device 14 and/or remote monitoring system 16. For embodiments in which processing is performed locally, remote monitoring device 12 includes a processor, storage medium and communication interface (shown in more detail in FIGS. 10a-10b). Monitored EKG signals are processed locally by the processor, with results stored to the storage medium or communicated via the communication interface to intermediate device 14. In embodiments in which two monitoring device are affixed to patient P, the monitoring devices may be configured to communicate measured EKG signals to one another for local processing of the EKG signals prior to communication to intermediate device 14. In still other embodiments, monitored EKG signals are communicated directly (e.g., unprocessed) to intermediate device 14.

In the embodiment shown in FIG. 1, intermediate device 14 includes antenna 20, processor 22 and storage medium 24. Antenna 20 is configured to communicate wirelessly with monitoring device 12 via wireless communication path 18, and may include bi-directional communication. For example, as discussed in more detail below, in one embodiment intermediate device 14 provides timing signals to monitoring device 12 (as well as a second monitoring device) that allows the monitored EKG signals provided by the respective monitoring devices to be aligned based on timestamps provided by the timing signals. In addition, monitoring device 12 provides EKG signals and/or processed data to intermediate device 14 via antenna 20. Upon reception, processor 22 and storage medium 24 may provide processing of the received EKG data and/or further processing of processed data received from monitoring device 12. In turn, intermediate device 14 communicates EKG signals, processed data, and/or alerts to remote monitoring system 16.

Remote monitoring system 16 is connected to communicate via either wired or wireless communication channel 26 with intermediate device 14. In the embodiment shown in FIG. 1, remote monitoring system includes processor 28, storage medium 30 and display 32. As discussed above, processing of monitored EKG signals may be performed locally by monitoring device 12, by intermediate device 14, or remotely by remote monitoring system 16. If done remotely at remote monitoring system 16, then EKG signals monitored by monitoring device 12 are communicated to remote monitoring system 16 via intermediate device 14. Processor 28 and storage medium 30 operate in conjunction to process the received EKG signals to detect attributes such as QT interval. Results of the analysis performed can then be displayed to a user or medical personnel via display 32.

Figure 2:
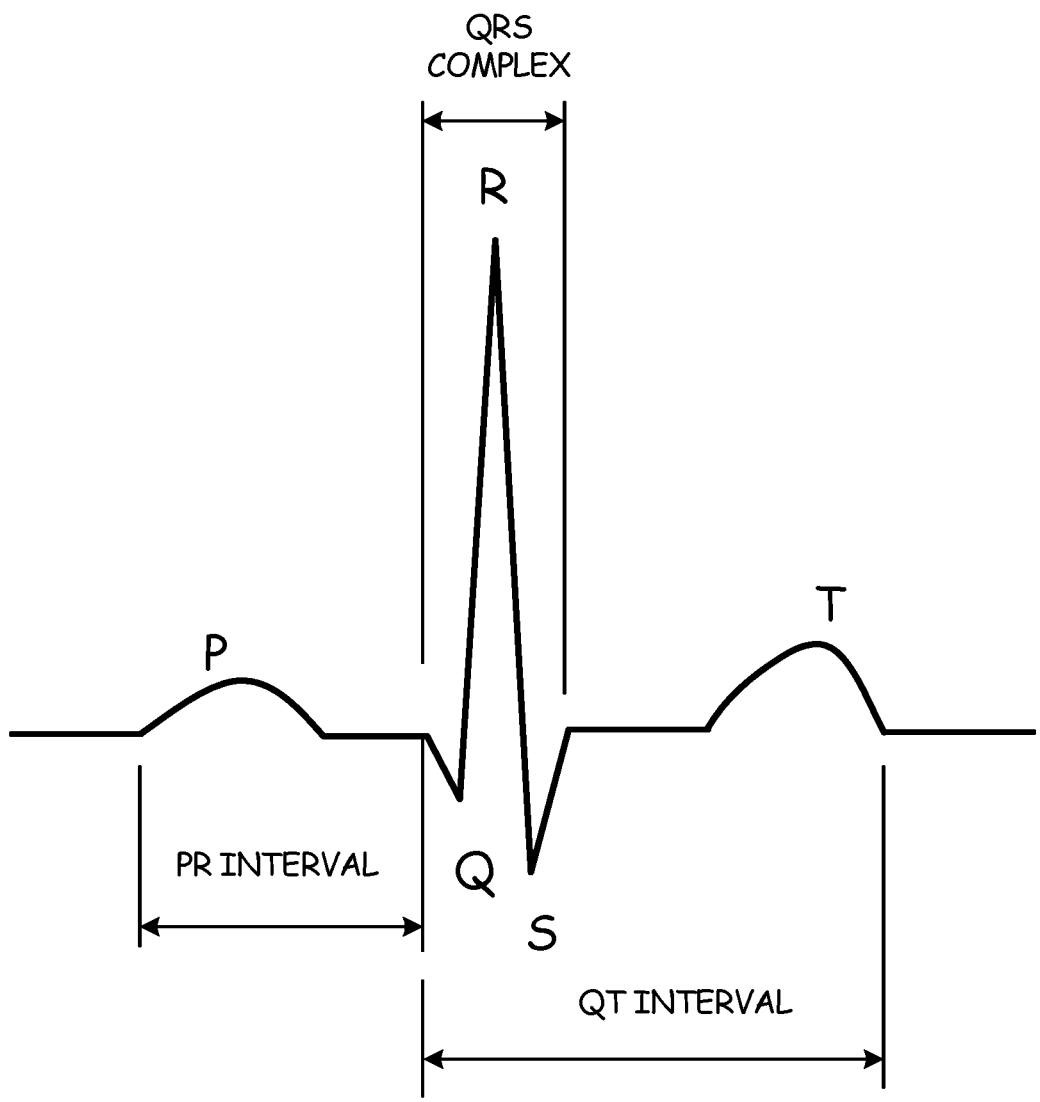
FIG. 2 is a graphical representation of an EKG signal that illustrates calculation of the QT interval according to an embodiment of the present invention

FIG. 2 is a graphical representation of an EKG signal that illustrates calculation of the QT interval according to an embodiment of the present invention. In the embodiment shown in FIG. 2, the EKG signal measured by monitoring device 12 (shown in FIG. 1) consists of three components or phases: the P-wave; the QRS complex (which is comprised of a Q-wave, an R-wave, and an S-wave); and the T-wave. The QT interval is measured from the onset of the QRS complex to the end of the T-wave. Accurate measurement of the QT interval therefore depends on accurately detecting the various components of the EKG signal and in particular in identifying the onset of the QRS complex and the end of the T-wave.

Figure 3:
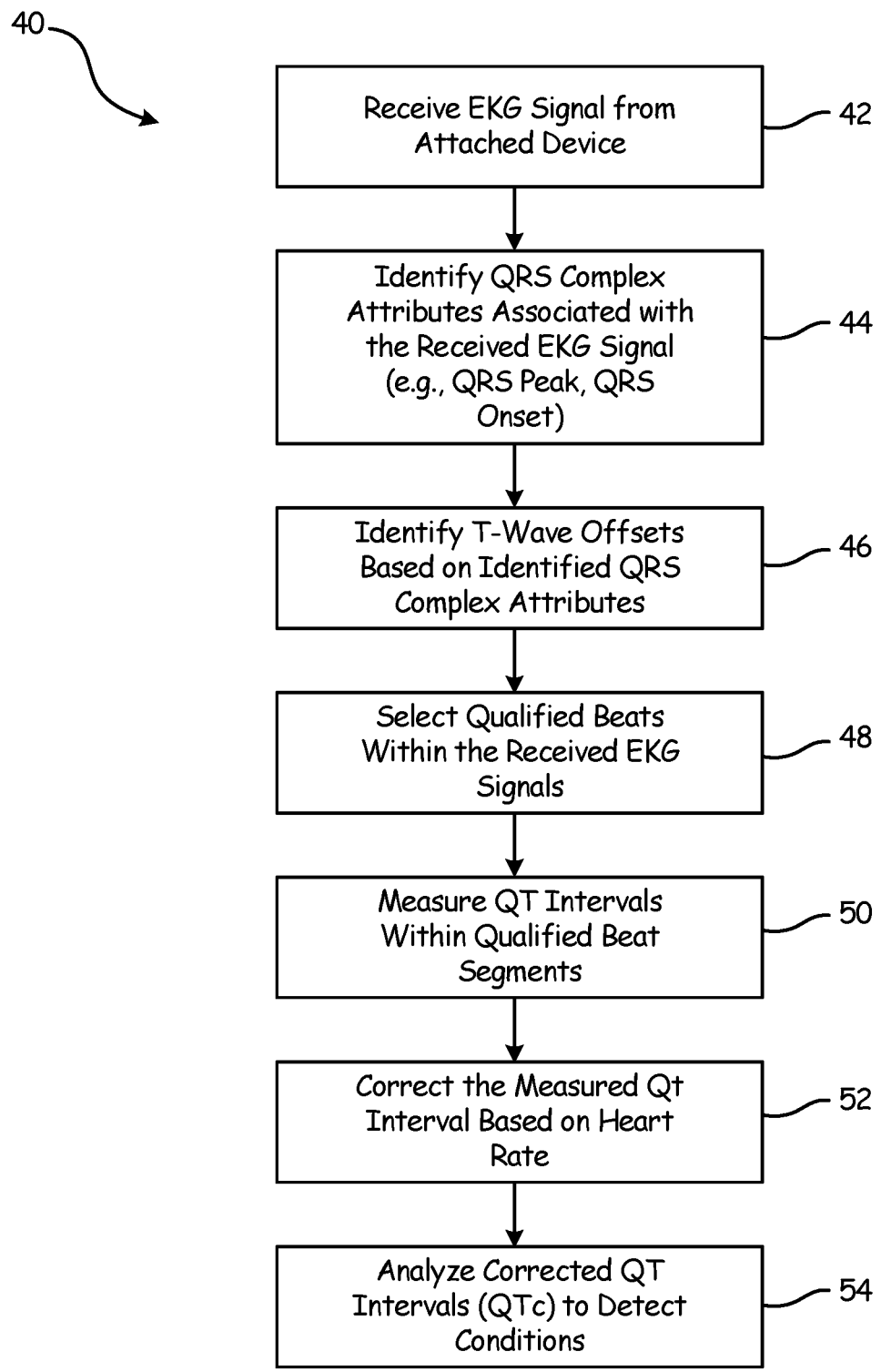
FIG. 3 is a flowchart that illustrates calculation of the QT interval based on a received EKG signal according to an embodiment of the present invention.

FIG. 3 is a flowchart that illustrates steps performed in measuring the QT interval associated with a particular patient. Steps described with respect to method 40 may be performed at a single location (e.g., monitoring device 12, intermediate device 14, or remote monitoring station 16) or may be split between a plurality of locations with some steps being performed by monitoring device 12, while others are performed by intermediate device 14 and/or remote monitoring system 16.

At step 42, an EKG signal is received for analysis. The EKG signal is comprised of a plurality of cardiac cycles, each cycle comprised of the P-wave, QRS complex, and T-wave components discussed above. At step 44, QRS locations of the EKG signal are identified, including the peak of the QRS complex (iRpk) and the QRS onset (iRon). In addition, at step 44 additional aspects or attributes associated with the EKG signal may be determined, such as heart rate (R-R) of the patient calculated based on the intervals between the detected QRS peaks and noise values. For each of the beats identified as comprising a large noise component, a beat-wise noise flag may be set that indicates analysis cannot be conducted on the identified heartbeat or cycle. Components of the EKG signal detected at step 44 are stored or otherwise retained for use in subsequent steps.

At step 46, the T-wave offset (iToff) is located for each cardiac cycle or beat based on the QRS complex aspects identified at step 42. A number of algorithms may be utilized to detect the T-wave within an EKG signal, and in particular the T-wave offset value (iToff). In one embodiment, this includes generating a T-wave offset estimate (iToff_estimate) based on a look-up table that utilizes the measured heart rate value determined at step 44. As the name implies, the T-wave offset estimate iToff_estimate is an estimate of where the T-wave offset is likely to be located based on the patient's heart rate. The faster the heart rate of the patient, the closer the T-wave offset is likely to be located to the QRS peak. The T-wave offset estimate iToff_estimate is used to define a T-wave offset detection window that represents the window of time wherein subsequent analysis will be performed to locate the actual T-wave offset iToff. In one embodiment, the T-wave offset detection window is defined as between the T-wave offset estimate iToff_estimate plus 50 milliseconds (ms). Within the T-wave offset detection window, peak and valley (maximum and minimum values) are located, with the valley representing the T-wave offset iToff. Depending on the location and orientation of the monitoring device, in some embodiments the T-wave offset iToff may be inverted. However, this can be overcome by utilizing the absolute values of the calculated peak and valleys and/or utilizing accelerometer values to determine the orientation of the monitoring device and whether values need to be inverted as a result. If the T-wave offset iToff cannot be detected, then a T-wave offset value is not asserted for that beat and it is discarded for analysis purposes.

At step 48, qualified beats within the EKG signal are identified that are appropriate for QT interval analysis. In one embodiment, this means analysis of beats to identify beats that are non-noisy. In this embodiment, beat-wise noise flags identified at step 44 are utilized to determine whether a particular segment is noisy or not. In one embodiment, a segment is identified as non-noisy if a requisite number of consecutive beats are identified as non-noisy. For example, in one embodiment, a segment is identified as non-noisy if five or more consecutive beats are identified as non-noisy (e.g., no beat-wise noise flags set). In other embodiments, other thresholds may be utilized to determine whether a segment is noisy and other criterion may be utilized to determine whether a segment of groups is well-suited to QT interval analysis, such as time of day, activity level of the patient, orientation of the patient, heart rate of the patient, etc.

At step 50, a QT interval is measured with respect to one or more beats within identified qualified (e.g., non-noisy)

segments. Measurement of the QT interval may include measurement of two or more QT intervals associated with two or more beats within the qualified segment and averaging of the measured QT intervals, or measurement of a single QT interval within the qualified segment. In one embodiment, in addition to identifying qualified segments, additional requirements are imposed when measuring a QT interval associated with a particular beat. For example, in one embodiment QT intervals are only measured for beats that are preceded by a non-noisy beat. As a result, the first beat identified in a non-noisy segment—if preceded by a noisy beat—will not be utilized to measure a QT interval.

As discussed above, the QT interval is measured from the onset of the QRS complex to the offset or end of the T-wave (e.g., iQT=iToff−iRon). In one embodiment, an additional requirement on whether a QT interval is measured for a particular beat is whether attributes of the beat required to measure the QT interval—namely the onset of the QRS complex and end of the T-wave—are detectable or otherwise distinguishable in the monitored EKG signal. If these attributes cannot be discerned from the EKG signal, even if found in a non-noisy segment and meeting the other requirements, the beat is discarded and not used for measurement of the QT interval.

At step 52, the measured QT interval is corrected based on the heart rate of the patient. A number of well-known algorithms may be utilized to correct the measured QT interval, including for example those developed by Bazett, Fridericia, and Framingham, reproduced below:

$$QTc_{Bazett}=QT/RR^{0.5}$$

$$QTc_{Fridericia}=QT/RR^{0.33}$$

$$QTc_{Framingh}=QT+1.54*(1-RR)$$

In one embodiment, if more than one corrected QT interval is calculated for a measured QT interval, the corrected QT intervals are averaged together to provide an averaged calculated QT interval. In some embodiments, a plurality of QT intervals are measured, and for each measured QT interval a corrected QT interval is calculated, resulting in a plurality of corrected QT intervals provided for analysis at step 54.

At step 54, the corrected QT interval(s) are analyzed to detect conditions such as Long QT Syndrome (LQTS). In the simplest embodiment, all corrected QT intervals are utilized in the analysis. In other embodiments, filters may be utilized to select particular corrected QT intervals for analysis based on one or more other physiological parameters of the patient, such as instantaneous heart rate, average heart rate, activity level of the patient, ongoing arrhythmia information, etc.

Analysis of the corrected QT interval may include—in the simplest embodiment—a comparison of the corrected QT interval to a threshold value. If the corrected QT interval is greater than the threshold value, this is indicative of a possible LQTS condition and may result in a flag being set or notification sent to attending medical personnel. In other embodiments, additional physiological parameters or conditions are accounted for in analyzing the corrected QT interval.

In this way, EKG signals monitored by an adherent device can be automatically analyzed to detect conditions related to the QT interval. One benefit of this arrangement is that monitoring may occur over several days or weeks, with QT intervals (and corrected QT intervals) being calculated and monitored over this time period. This allows not only for detection of extreme QT interval events that occur infrequently and may not be detected in a shorter duration monitoring period, but also allows for monitoring of trends in the change of the monitored QT interval over a period of time. In addition, the described system allows the patient's QT interval to be monitored during different physiological states, such as while active.

Figure 4:
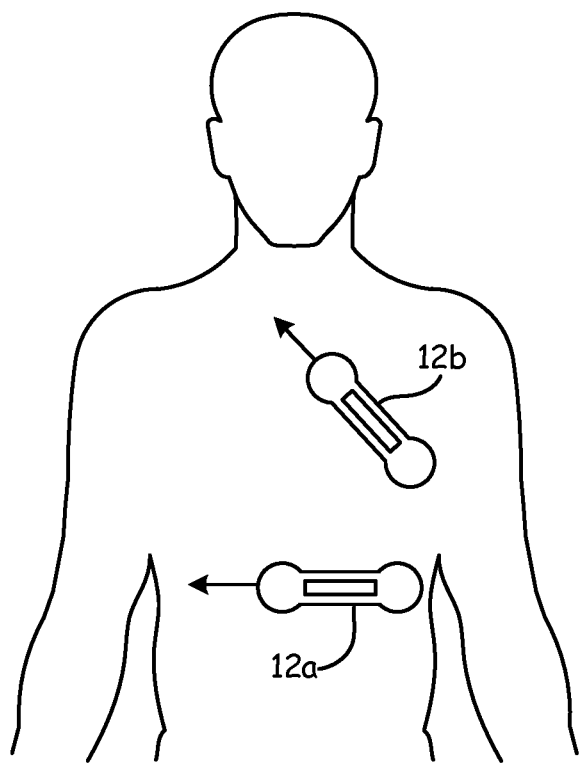
FIG. 4 illustrates placement of two monitoring devices capable of measuring electrocardiogram (EKG) signals according to an embodiment of the present invention.

FIG. 4 illustrates placement of monitoring devices 12a and 12b on patient P according to embodiments of the present invention. In contrast with the embodiments described with respect to FIGS. 2-3, in which the QT interval is determined based on measurements received from a single monitoring device—selectively located on one portion of the patient's body—the embodiments described with respect to FIGS. 4-5 rely on at least two EKG signals measured by a monitoring device or devices at different locations. As described in more detail below, one benefit of utilizing two EKG signals measured at different locations is that each EKG signal has different attributes (e.g., clearly defined QRS onset information) that when combined allow the QT interval to be accurately determined. In addition, movement of monitoring device or devices—and as a result, movement of associated electrodes—can negatively impact the quality of EKG signals monitored. This issue is particularly problematic with monitoring of a patient outside of a hospital setting in which the patient is performing daily activities. Movement of the monitoring device and associated electrodes results in noise and/or movement artifacts being introduced into the EKG signals. A benefit of utilizing more than one monitoring device is that the noise signals associated with multiple EKG signals—which are independent of one another—will tend to average out over time.

In the embodiment shown in FIG. 4, first monitoring device 12a is placed on the abdomen of patient P while second monitoring device 12b is placed on the chest of patient P. First monitoring device 12a is oriented in a horizontal direction—as indicated by the direction of the arrow adjacent to monitoring device 12a. The position of monitoring device 12a is referred to as a first lead position and generates in response a first EKG signal EKG_a. Second monitoring device 12b is located on the chest of patient P and oriented at an angle of approximately 45 degrees to monitoring device 12a. The position of monitoring device 12b is referred to as a second lead position and generates in response a second EKG signal EKG_b. In one embodiment, first and second monitoring devices 12a and 12b are adhered to patient P at approximately the same time, and collect data simultaneously from the patient. However, in other embodiments, first and second monitoring devices may be adhered to patient P at times that only partially overlap with one another. In still other embodiments, a single monitoring device 12 may be placed at the first lead position for a first period of time and then moved to the second lead position for a second period of time. Similarly, first monitoring device 12a may be located at first lead position for a first period of time and then a second monitoring device 12b may be located at second lead position at a second period of time different from and not co-extensive with the first period of time. In each of these embodiments however, first and second EKG signals are measured from at least first and second locations. This is in contrast with the embodiments described with respect to FIGS. 2 and 3, in which an EKG signal measured from a single location is used to detect the QT interval. Although reference is made throughout with respect to the EKG signals monitored at the positions illustrated in FIG. 4, monitoring devices 12a and 12b may be located in other positions on patient P.

Figure 5:
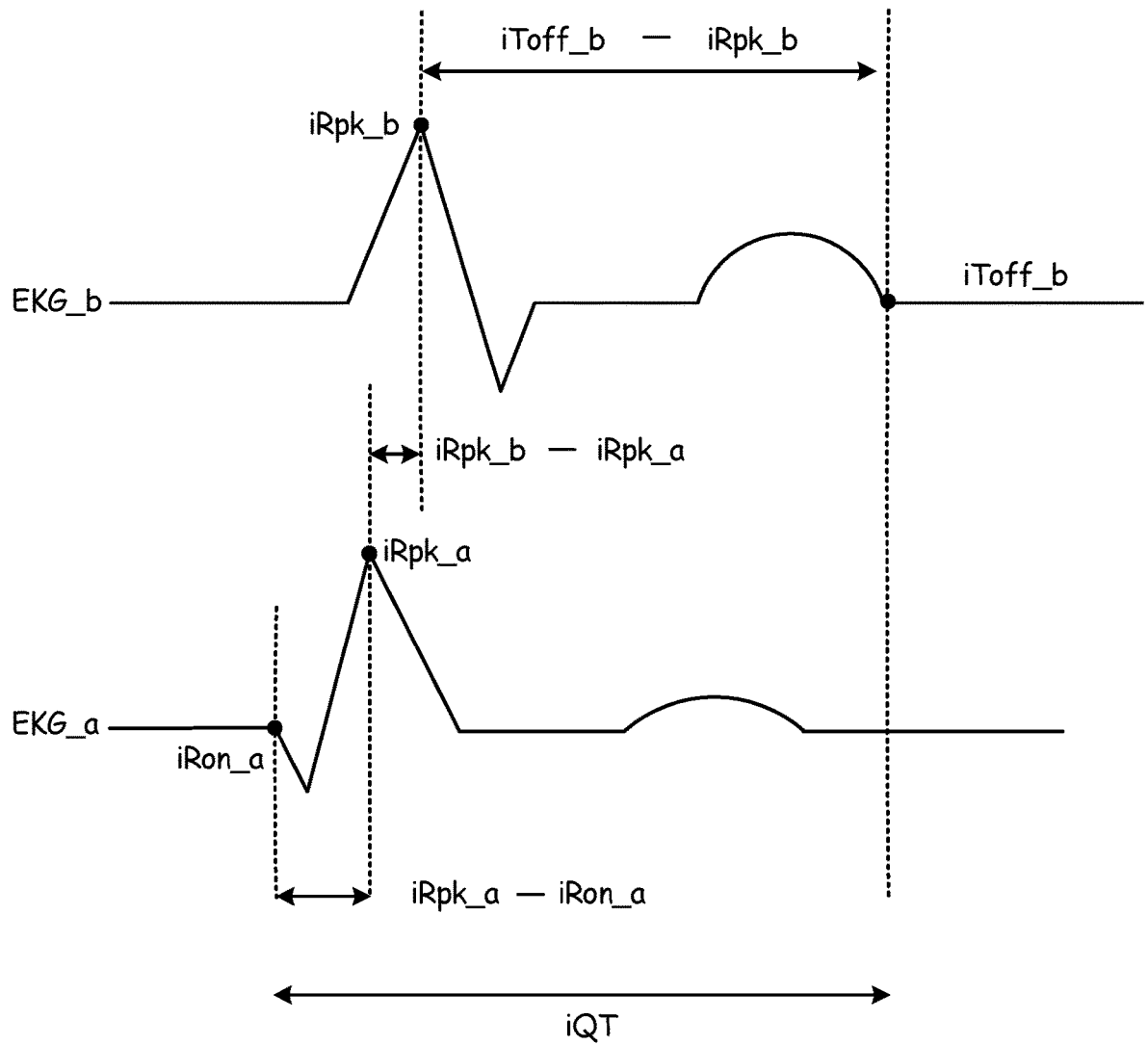
FIG. 5 is a graphical representation of first and second EKG signals used to calculate a QT interval according to an embodiment of the present invention

FIG. 5 illustrates calculation of the QT interval according to an embodiment of the present invention in which first and second EKG signals are utilized in combination with one another. In the embodiment shown in FIG. 3, monitoring device 12b located on the patient's chest provides the EKG signal labeled EKG_b, illustrated in the top portion of FIG. 5. Monitoring device 12a located on the patient's abdomen provides the EKG signal labeled EKG_a, illustrated in the bottom portion of FIG. 5.

Although both monitoring devices 12a and 12b are monitoring the same cardiac cycle, the difference in location and orientation provides a different "view" of that cardiac activity which is reflected in the respective EKG signals of each. For example, with respect to second EKG signal EKG_b, the onset of the QRS complex is not easily distinguished or detectable, but the end of the T-wave signal is well distinguished. In contrast, with respect to the first EKG signal EKG_a, the onset of the QRS complex is well distinguished, but the end of the T-wave signal is less distinguished. Because the QT interval is measured as the interval of time between the onset of the QRS complex and the end or offset of the T-wave, it is important to accurately distinguish and detect both the onset of the QRS complex and the end of the T-wave. To this end, the present invention utilizes characteristics of both the first EKG signal EKG_a and the second EKG signal EKG_b in order to accurately measure the QT interval.

In the embodiment shown in FIG. 5, the QT interval is determined by measuring the interval of time between the peak of the QRS complex (iRpk_b) and the end of the T-wave (iToff_b) associated with the second EKG signal EKG_b as well as the interval of time between the onset of the QRS complex (iRon_a) and the peak of the QRS complex (iRpk_a) associated with the first EKG signal. The interval between the peak of the QRS complex and the end of the T-wave associated with the second EKG signal is illustrated graphically in the top waveform of FIG. 3, and can be expressed as interval_b=iToff$_b$–iRpk_b. The interval between the onset of the QRS complex and the peak of the QRS complex associated with the first EKG signal is illustrated graphically in the bottom waveform of FIG. 3, and can be expressed as: interval_a=iRpk_a–iRon_a. The QT interval is defined as the sum of the first and second intervals, which can be expressed as: iQT=interval_a+interval_b.

The common denominator in the measured intervals combined to form the QT interval is the measured peak of the QRS complex of the first and second EKG signals. For this reason, it is important that the measured QRS peaks of the first and second EKG signals are aligned with one another. In embodiments in which monitoring devices 12a and 12b receive timing information from a timing server (e.g., intermediate device 14), the respective first and second EKG signals will have globally synchronized time-stamps that do not require additional alignment of the QRS peaks. However, if the monitoring devices are not synchronized via a global timing signal, then alignment between the first and second EKG signals can be verified by detecting the interval between the respective peaks and comparing the detected interval to a threshold value. In the embodiment shown in FIG. 5, this alignment check is illustrated graphically by the interval between the respective peaks and can be expressed as: iRpk$_b$–iRpk$_a$<threshold. If the difference in QRS peak values is greater than the threshold value, this indicates that the QRS peaks are not well aligned and therefore that the calculated QT interval may be inaccurate as a result. In one embodiment, if the interval between the respective peaks is greater than the threshold value, the calculated QT interval is discarded as inaccurate. In another embodiment, if the interval between the respective peaks is greater than the threshold value, the calculated QT interval is modified to account for the interval between the respective peaks. For example, the interval between the respective peaks (i.e., iRpk_b–iRpk_a) can be subtracted from the calculated QT interval, with the result representing the new QT interval. Because the QT interval is related to the heart rate of the patient, in one embodiment it is further required that two or more QRS peaks be aligned with one another to calculate a QT interval. This requirement ensures that underlying heart rates associated with the first and second EKG signals are approximately equal to one another, and as result the effect of heart rate on the QT intervals associated with each EKG signal will be the same. This requirement is particularly important for comparison of EKG signals not measured at the same time, but for which QRS peaks have been aligned for purposes of measuring QT intervals.

Figure 6:
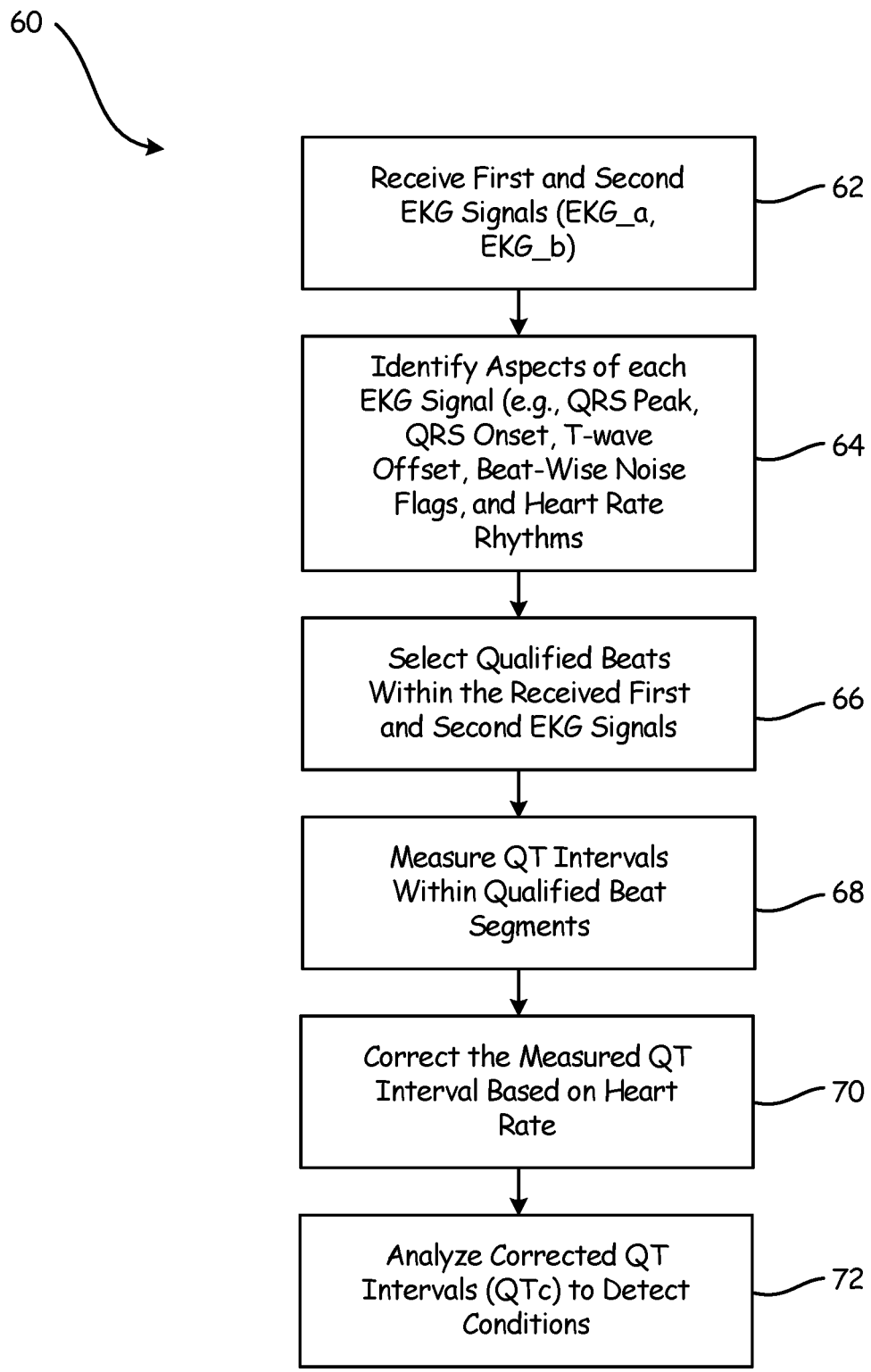
FIG. 6 is a flowchart illustrating a method of calculating QT intervals based on a two EKG signals received from first and second monitoring devices, respectively, synchronized in time with one another according to an embodiment of the present invention.

FIG. 6 is a flowchart illustrating a method of calculating QT intervals based on a two or more EKG signal received from monitoring devices according to an embodiment of the present invention. In particular, in the embodiment shown in FIG. 6, global timing information is provided by intermediate device 14 (shown in FIG. 1) or some other device that allows global time stamps to be associated with both the first EKG signal EKG_a and the second EKG signal EKG_b. As a result, the method described with respect to FIG. 6 does not require additional steps to align the peaks of the QRS complexes, but can instead rely on the global time-stamps to align the first and second EKG signals EKG_a and EKG_b.

At step 62, first and second EKG signals EKG_a and EKG_b are received for analysis. Each EKG signal is comprised of a plurality of cardiac cycles, each cycle comprised of the P-wave, QRS complex, and T-wave components discussed with respect to FIG. 2 above. At step 64, QRS and T-wave locations of the EKG signal are identified, including the peak of the QRS complex (iRpk), the QRS onset (iRon), and the T-wave offset (iToff). Although grouped with identification of the QRS onset and peak, identification of the T-wave offset (iToff) may include steps described with respect to FIG. 3, in which a T-wave offset estimate (iToff_estimate) is selected from a look-up table based on the patient's heart rate. The T-wave offset estimate iToff_estimate is used to define a T-wave offset detection window that represents the window of time wherein subsequent analysis will be performed to locate the actual T-wave offset iToff. Within the T-wave offset detection window, peak and valley (maximum and minimum values) are located, and depending on morphology the T-wave offset iToff is detected.

In addition to these attributes, additional attributes associated with each EKG signal may be detected at step 64 including heart rate (R-R) and noise values (e.g., beat-wise noise flags). Monitored attributes of the EKG signal detected at step 64 are stored or otherwise retained for use in subsequent steps.

At step 66, beats within the first and second EKG signals are analyzed to select qualified beats (e.g., beats suitable for subsequent analysis of QT intervals). For example, in one embodiment beats are analyzed to identify non-noisy segments. As discussed above with respect to FIG. 3, beat-wise noise flags are utilized to determine whether a particular segment is noisy or not. A segment can be identified as non-noisy if a requisite number of consecutive beats are identified as non-noisy. For example, in one embodiment, a segment is identified as non-noisy if five or more consecutive beats are identified as non-noisy (e.g., no beat-wise noise flags set). In other embodiments, other thresholds may be utilized to determine whether a particular segment is noisy or not. In addition to noise levels, identification of qualified beats may also be predicated on other monitored parameters associated with patient P, such as time of day measurement are taken, activity level of the patient, and underlying average heart rate of the patient. For example, in some embodiments it may be desirable to calculate QT intervals during times of patient activity (or conversely, rest).

In one embodiment, a determination of qualified beats performed at step 66 requires aligned segments of the first and second EKG signals (EKG_a and EKG_b) to both be qualified (e.g., non-noisy) before a particular segment is identified as qualified for subsequent analysis. That is, if a segment of beats associated with the first EKG signal EKG_a is non-noisy, but the corresponding segment of beats associated with the second EKG signal EKG_b (e.g., measured at the same time) are noisy, then at step 66 both segments may be disqualified.

At step 68, QT intervals are measured based on the qualified beat segments associated with the first and second EKG signals EKG_a and EKG_b. As described in with respect to FIG. 5, measurement of the QT interval includes measuring a first interval with respect to the first EKG signal EKG_a, and a second interval with respect to the second EKG signal EKG_b. The QT interval iQT is represented by the sum of the first and second intervals. In particular, in the embodiment described with respect to FIG. 5 the second EKG signal EKG_b is utilized to measure the interval between the peak of the QRS complex (iRpk_b) and the T-wave offset (iToff_b). The first EKG signal EKG_a is utilized to measure the interval between the onset of the QRS complex (iRon_a) and the peak of the QRS complex (iRpk_a). The sum of these intervals represents the interval from the onset of the QRS complex to the offset of the T-wave, which represents the QT interval.

As described with respect to FIG. 3, above, measurement of the QT interval may include measurement of two or more QT intervals associated with two or more beats within a non-noisy segment and averaging of the measured QT intervals, or measurement of a single QT interval within the non-noisy segment. Also described with respect to FIG. 3, additional requirements may be imposed on which beats within a non-noisy segment are utilized to measured QT intervals. For example, in one embodiment QT intervals are only measured for beats that are preceded by a non-noisy beat. As a result, the first beat identified in a non-noisy segment—if preceded by a noisy beat—will not be utilized to measure a QT interval. In addition, whether a QT interval is measured for a particular beat is further predicated on whether the attributes used to calculate the interval—namely the onset of the QRS complex and end of the T-wave—are detectable or otherwise distinguishable in the monitored EKG signal. If these attributes cannot be discerned from the EKG signal, even if found in a non-noisy segment and meeting the other requirements, the beat is discarded and not used for measurement of the QT interval.

A benefit of the embodiment described with respect to FIG. 6, is because the EKG signals received from the monitoring devices include synchronized timing information, the respective EKG signals can be aligned based on the timing information and does not require additional processing to align the first and second EKG signals.

At step 70, the measured QT interval or intervals are corrected based on the heart rate associated with the qualified beats. As described with respect to FIG. 3, above, a number of well-known algorithms may be utilized to correct the measured QT interval, including for example those developed by Bazett, Fridericia, and Framingham. In one embodiment, if more than one corrected QT interval is calculated for a measured QT interval, the corrected QT intervals are averaged together to provide an averaged calculated QT interval. In some embodiments, a plurality of QT intervals are measured, and for each measured QT interval a corrected QT interval is calculated, resulting in a plurality of corrected QT intervals provided for analysis at step 72.

At step 72, the corrected QT interval(s) are analyzed to detect conditions such as Long QT Syndrome (LQTS). In the simplest embodiment, all corrected QT intervals are utilized in the analysis. In other embodiments, filters may be utilized to select particular corrected QT intervals for analysis based on one or more other physiological parameters of the patient, such as instantaneous heart rate, average heart rate, activity level of the patient, ongoing arrhythmia information, etc.

As described with respect to FIG. 3, above, analysis of the corrected QT interval may include—in the simplest embodiment—a comparison of the corrected QT interval to a threshold value. If the corrected QT interval is greater than the threshold value, this is indicative of a possible LQTS condition and may result in a flag being set or notification sent to attending medical personnel. In other embodiments, additional physiological parameters or conditions are accounted for in analyzing the corrected QT interval.

Figure 7:
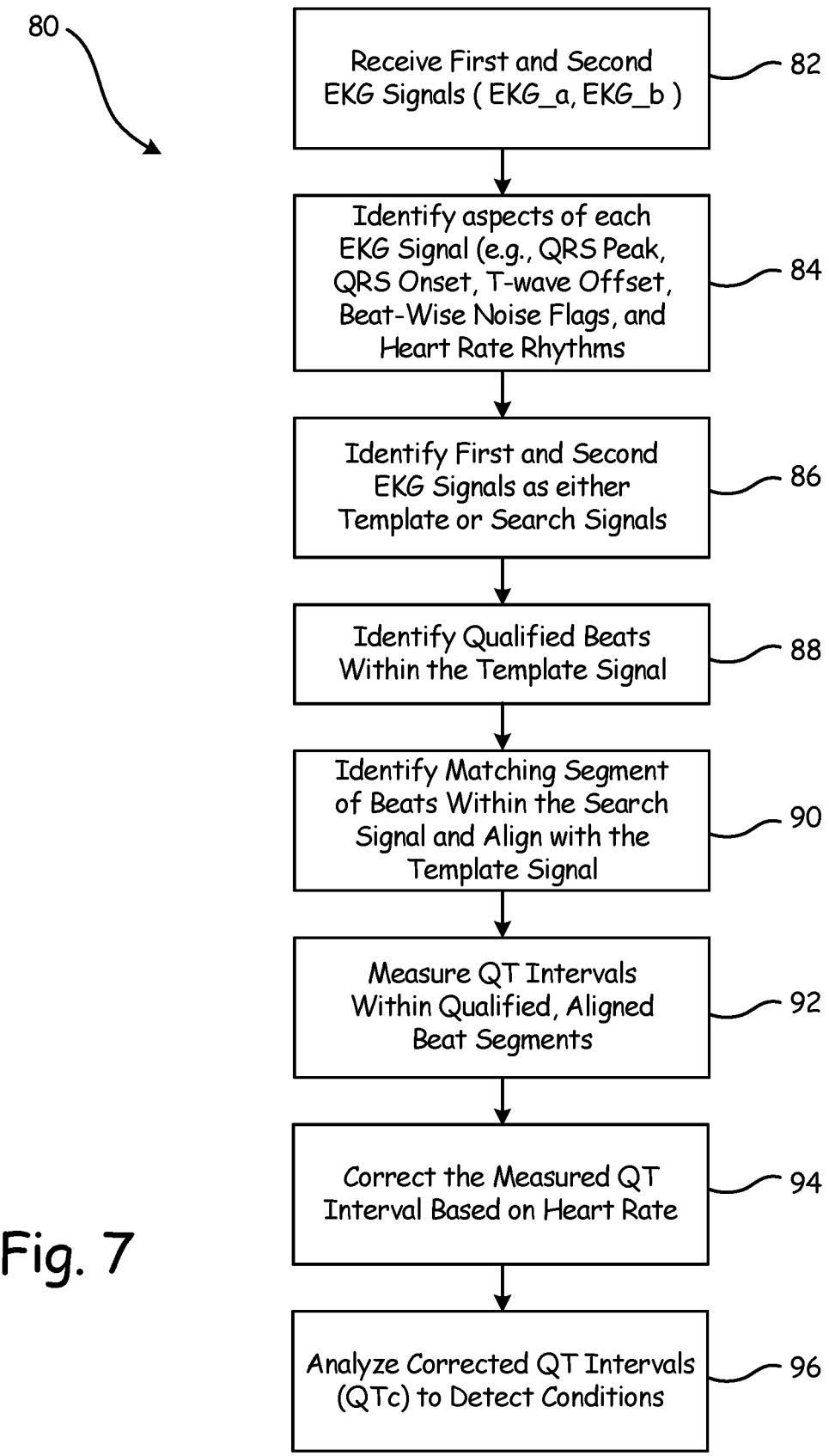
FIG. 7 is a flowchart illustrating a method of calculating QT intervals based on two EKG signals received from first and second devices, respectively, not synchronized in time with one another according to an embodiment of the present invention.

FIG. 7 is a flowchart illustrating a method of calculating QT intervals based on two EKG signals received from a pair of devices that do not share synchronized global time stamps according to an embodiment of the present invention. In contrast with the embodiment described with respect to FIG. 6, in which time information received by monitoring devices 12a and 12b allowed EKG signals to be aligned based on time signals, the embodiment described with respect to FIG. 7 allows first and second EKG signals to be aligned despite the lack of global timing information. The EKG signals illustrated graphically with respect to FIG. 5 are referred to again with respect to the embodiment described with respect to FIG. 7.

At step 82, first and second EKG signals EKG_a and EKG_b are received for analysis. Each EKG signal is comprised of a plurality of cardiac cycles, each cycle comprised of the P-wave, QRS complex, and T-wave components discussed with respect to FIG. 2 above. At step 84, QRS and T-wave locations of the EKG signal are identified, including the peak of the QRS complex (iRpk), the QRS onset (iRon), and the T-wave offset (iToff). Although grouped with identification of the QRS onset and peak, identification of the T-wave offset (iToff) may include steps described with respect to FIGS. 3 and 6, in which a T-wave offset estimate (iToff_estimate) is selected from a look-up table based on the patient's heart rate. The T-wave offset estimate iToff_estimate is used to define a T-wave offset detection window that represents the window of time wherein subsequent analysis will be performed to locate the actual T-wave offset iToff. Within the T-wave offset detection window, peak and valley (maximum and minimum values) are located, and depending on morphology the T-wave offset iToff is detected.

In addition to these attributes, additional attributes associated with each EKG signal may be detected at step 84 including heart rate (R-R) and noise values (e.g., beat-wise noise flags). Monitored attributes of the EKG signal detected at step 84 are stored or otherwise retained for use in subsequent steps.

At step 86, a template signal is selected from the first and second EKG signals. The selection is arbitrary, and either the first EKG signal or the second EKG signal may be identified as the template signal. The remaining EKG signal is identified as the search signal. For the purposes of this discussion, the first EKG signal EKG_a is identified as the template signal and the second EKG signal EKG_b is identified as the search signal.

At step 88, qualified beats are detected within the template signal (e.g., first EKG signal EKG_a). The criterion for selecting qualified one or more qualified segments of beats is similar to that utilized to detect qualified beats described with respect to FIGS. 3 and 5. In particular, non-noisy segments are selected based on the beat-wise noise flags associated with each beat. In addition, heart rate variation of beats within a segment may be used as a criterion, wherein segments with low heart rate variation are desirable. In one embodiment, segments with heart rate variation greater than five beats-per-minute (bpm) are discarded. This criterion is particularly important when lining up segments from the first EKG signal and second EKG signal collected at or measured at different instances of time. Variation in heart rate makes it more difficult to find a matching segment within the search signal that can be aligned with the template signal.

At step 90, having selected one or more qualified segments of beats within the template signal, a matching sequence or segment of beats is located within the search signal for each template signal segment. In one embodiment, matches are located based on an algorithm that seeks to align QRS peaks between the template signal and the search signal. Having identified QRS peak information at step 84 for both the template and search signals, this information is utilized to match segments between the template signal and the search signal according to selected criterion. For example, in one embodiment a segment is considered matching only if the QRS peaks from each are within a certain time interval of one another (e.g., 0.01 seconds) and a minimum number of QRS peaks are aligned with one another (e.g., 60%). Note that alignment of segments does not necessarily imply that the respective segments were collected at the same time. That is, a template signal segment may be aligned with a segment of the search signal measured at a wholly different instance in time. Qualifying template string segments based in part on lack of variation in the heart rate makes it substantially easier to locate matching search string segments. Because the QRS peaks or a substantial number of the QRS peaks between matched segments need to be in alignment, it reasons that the matching segments will share relatively similar heart rates.

In one embodiment, the alignment between segments in the template signal and the search signal is generated via an algorithm that selects suitable segments of beats (e.g., non-noisy) within the search single, and locates a best fit match within the template signal that satisfies the defined criterion. In some embodiments, no such match is located and the search signal segment is discarded so that another search signal segment can be tested. Various algorithms may be utilized to dynamically locate this best between the search signal segment and the template signal segment. For example, in one embodiment a b×b beat-lining up procedure is utilized that is given criterion described above (e.g., threshold of time between aligned QRS peaks, and percentage of peaks that need aligning) as input to find matches between the template signal and the search signal. The Needleman/Wunsch algorithm—originally designed to align protein or nucleotide sequences—may also be utilized to locate alignments between the respective template and search signals. In another embodiment, cross-correlation between the template and search signal may be utilized to align segments between the respective signals. The cross-correlation approach relies on variation in the template signal segment to locate matching segments in the search signal segments, and therefore may be more well-suited to instances in which the patient's heart rate is varying within a wider range.

At step 92, QT intervals are measured based on the aligned beat segments selected from the template signal and the search signal (e.g., first and second EKG signals EKG_a and EKG_b). Once aligned beat segments have been located, calculation of the QT interval proceeds as described with respect to the embodiment in FIG. 5. Measurement of the QT interval includes measuring a first interval with respect to the first EKG signal EKG_a, and a second interval with respect to the second EKG signal EKG_b. The QT interval iQT is represented by the sum of the first and second intervals. In particular, in the embodiment described with respect to FIG. 5 the second EKG signal EKG_b is utilized to measure the interval between the peak of the QRS complex (iRpk_b) and the T-wave offset (iToff_b). The first EKG signal EKG_a is utilized to measure the interval between the onset of the QRS complex (iRon_a) and the peak of the QRS complex (iRpk_a). The sum of these intervals represents the interval from the onset of the QRS complex to the offset of the T-wave, which represents the QT interval.

As described with respect to FIGS. 3 and 5, above, measurement of the QT interval may include measurement of two or more QT intervals associated with two or more beats within a non-noisy segment and averaging of the measured QT intervals, or measurement of a single QT interval within the non-noisy segment. Also described with respect to FIGS. 3 and 5, additional requirements may be imposed on which beats within a non-noisy segment are utilized to measured QT intervals. For example, in one embodiment QT intervals are only measured for beats that are preceded by a non-noisy beat. As a result, the first beat identified in a non-noisy segment—if preceded by a noisy beat—will not be utilized to measure a QT interval. In addition, whether a QT interval is measured for a particular beat is further predicated on whether the attributes used to calculate the interval—namely the onset of the QRS complex and end of the T-wave—are detectable or otherwise distinguishable in the monitored EKG signal. If these attributes cannot be discerned from the EKG signal, even if found in a non-noisy segment and meeting the other requirements, the beat is discarded and not used for measurement of the QT interval.

A benefit of the embodiment described with respect to FIG. 7, is that it may utilize EKG signals received from monitoring devices that are not synchronized with one another. As a result, monitoring devices 12a and 12b do not necessarily have to measure the respective EKG signals at the same time. In fact, in one embodiment a single monitoring device is utilized at two different locations, and matching segments from the EKG signals measured at each location are utilized to estimate the patient's QT interval.

At step 94, the measured QT interval or intervals are corrected based on the heart rate associated with the qualified beats. As described with respect to FIG. 3, above, a number of well-known algorithms may be utilized to correct the measured QT interval, including for example those developed by Bazett, Fridericia, and Framingham. In one embodiment, if more than one corrected QT interval is calculated for a measured QT interval, the corrected QT intervals are averaged together to provide an averaged calculated QT interval. In some embodiments, a plurality of QT intervals are measured, and for each measured QT interval a corrected QT interval is calculated, resulting in a plurality of corrected QT intervals provided for analysis at step 95.

At step 95, the corrected QT interval(s) are analyzed to detect conditions such as Long QT Syndrome (LQTS). In the simplest embodiment, all corrected QT intervals are utilized in the analysis. In other embodiments, filters may be utilized to select particular corrected QT intervals for analysis based on one or more other physiological parameters of the patient, such as instantaneous heart rate, average heart rate, activity level of the patient, ongoing arrhythmia information, etc.

As described with respect to FIG. 3, above, analysis of the corrected QT interval may include—in the simplest embodiment—a comparison of the corrected QT interval to a threshold value. If the corrected QT interval is greater than the threshold value, this is indicative of a possible LQTS condition and may result in a flag being set or notification sent to attending medical personnel. In other embodiments, additional physiological parameters or conditions are accounted for in analyzing the corrected QT interval.

Figure 8:
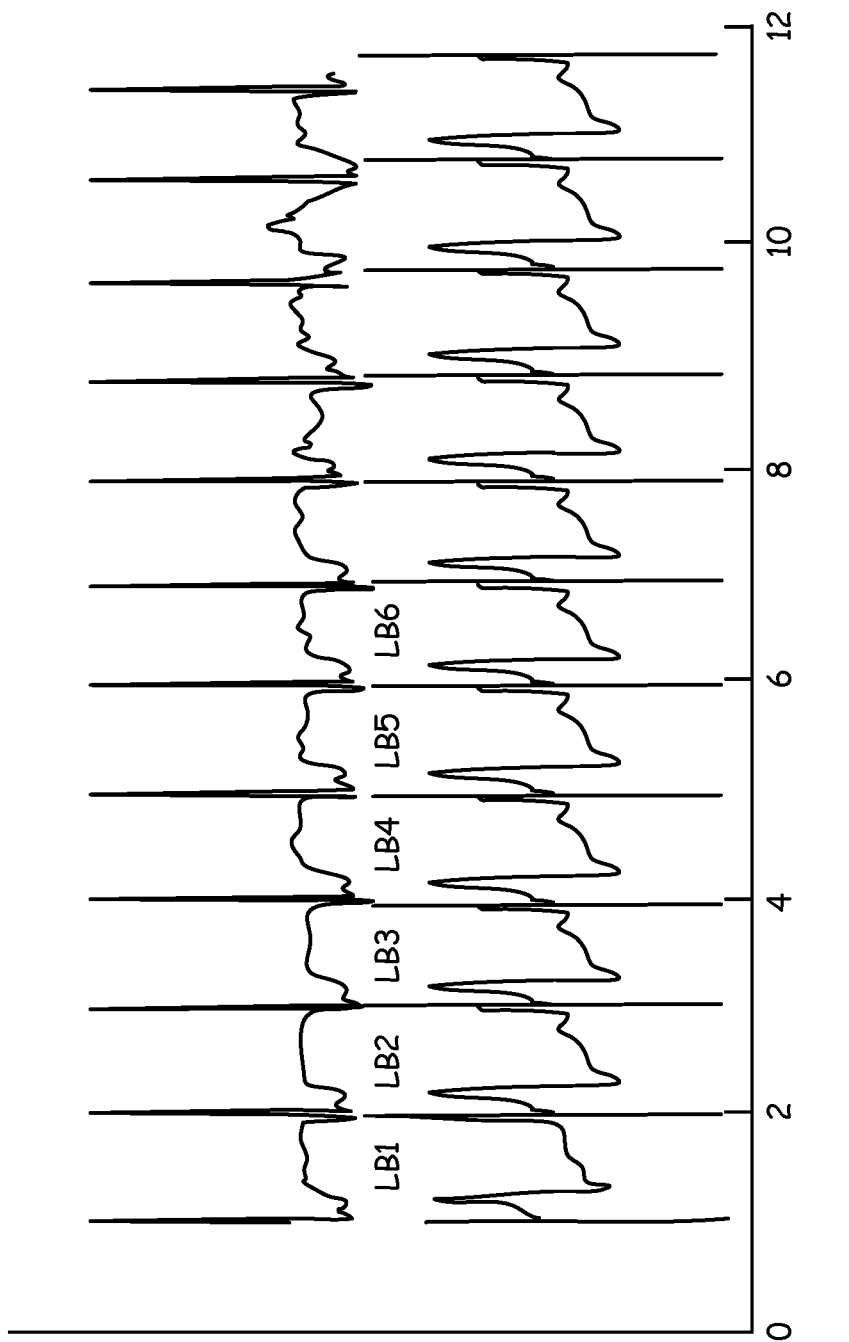
FIG. 8 is a waveform diagram illustrating matching of first and second waveform signals and calculation of QT intervals as a result of the matching according to embodiments of the present invention.

FIG. 8 is a waveform diagram illustrating matching of first and second waveform signals and calculation of QT intervals as a result of the matching according to embodiments of the present invention that utilize a template signal and a search signal to align EKG signals. In embodiments in which both EKG signals have global timing information received from a timing server (e.g., intermediate device 14 shown in FIG. 1), then alignment of the beats is not required because the timing information can be relied upon for this purpose. However, in the embodiment shown in FIG. 8, no timing information is provided and instead alignment of the beats using a template signal and a search signal is required.

In the embodiment shown in FIG. 8, a template signal is illustrated in the top waveform chart and a search signal is illustrated in the bottom waveform chart. In the graphical representation of the EKG signals, a number of cardiac cycles are illustrated and components of each cardiac cycle—including QRS and T-wave components, beat-wise noise flags, heart rate, etc.—are automatically identified. In addition, with respect to the template signal, qualified beats are detected as illustrated in FIG. 8 by beats LB1-LB6. In this embodiment, the prefix "LB" is an acronym for "lined beats", and represents those beats that are aligned for potential QT information extraction. Identification of qualified beats may be based on one or more criterion, including identification of non-noisy segments based on beat-wise noise flags, and relatively stable heart rate within the identified segment. In addition, other criterion such as time of day and/or activity level of the patient may further be utilized to determine whether a segment should utilized for QT interval analysis or not.

Having identified a qualified segment of beats (e.g., LB1-LB6) within the template signal, a matching sequence of beats is located within the search signal. The beats identified within the search signal are not required to have been measured contemporaneously with the aligned beats from the template signal, although in some applications it may be desirable that the aligned beats are selected from time periods of overlapping measurement of first and second EKG signals. One or more criterion may be utilized to determine whether a search signal segment matches a template signal segment. For example, as described with respect to the embodiment shown in FIG. 7, criterion such as a minimum threshold of time between aligned QRS peaks may be imposed to ensure alignment between the QRS peaks. In addition, criterion may include that a certain percentage of QRS peaks within a given segment must be aligned in order for the segment to qualify as properly aligned. In embodiments in which the heart rate of the template signal is relatively stable, it will often result in the search signal segment having a heart rate rhythm substantially equal to the heart rate of the template signal segment. In the embodiment shown in FIG. 8, a plurality of beats within the search signal have been aligned with the beats LB1-LB6 within the qualified template segment. In the embodiment shown in FIG. 8, the onset of QRS complexes within each beat are aligned with one another—as opposed to QRS peaks, which may also be utilized. The difference in location and orientation of the monitoring devices utilized to measure the first and second EKG signal (template and search signals, respectively) causes differences in the shape of the template signal and the search signal. Once aligned, the QT interval can be measured as described above and utilized to detect conditions such as long QT intervals. Although in order to qualify as aligned, the QRS peaks are the aligned beats are required to be within a defined threshold of one another (e.g., 0.01 seconds), small differences in alignment between the respective QRS peaks such as those shown in FIG. 8 can be accounted for by subtracting the difference in QRS peaks (e.g., iRpk_b−iRpk_a) from the measured QT interval.

Figure 9A:
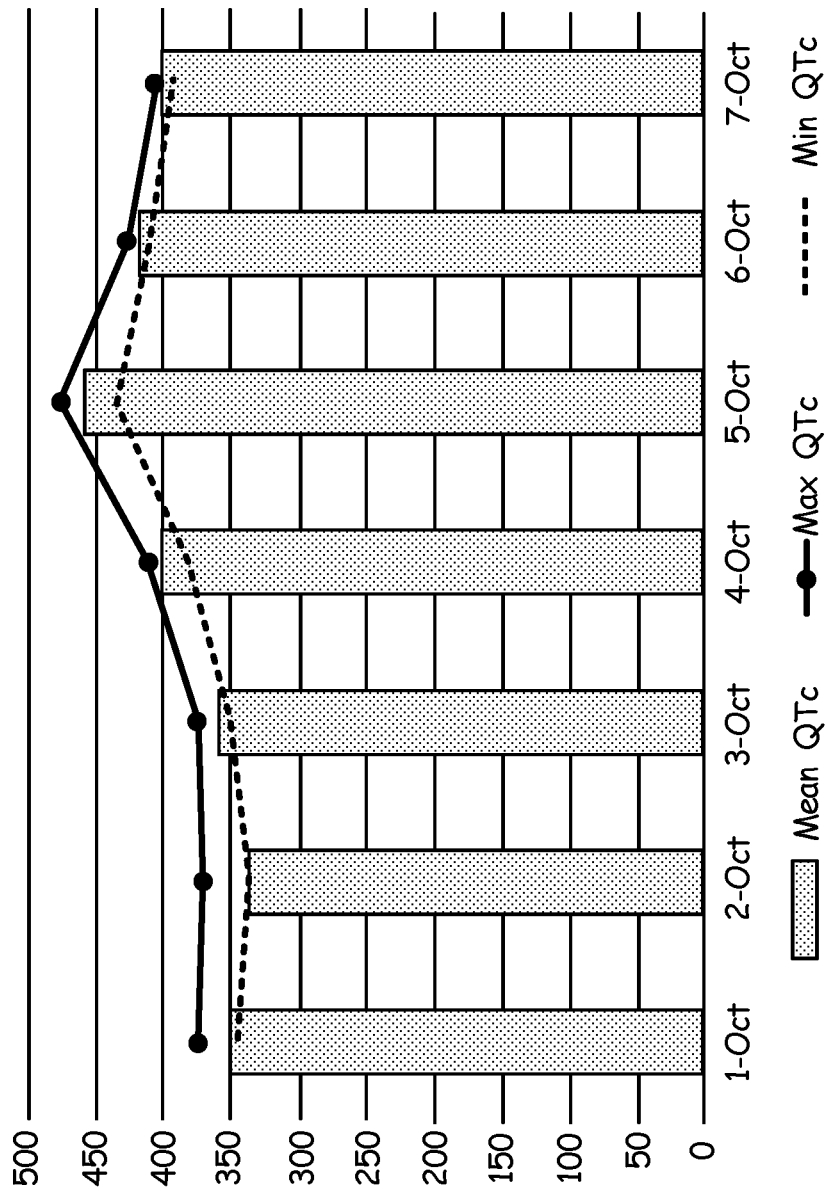
FIGS. 9A-9C are displays illustrating various methods of displaying measured QT interval data according to embodiments of the present invention.
Figure 9B:
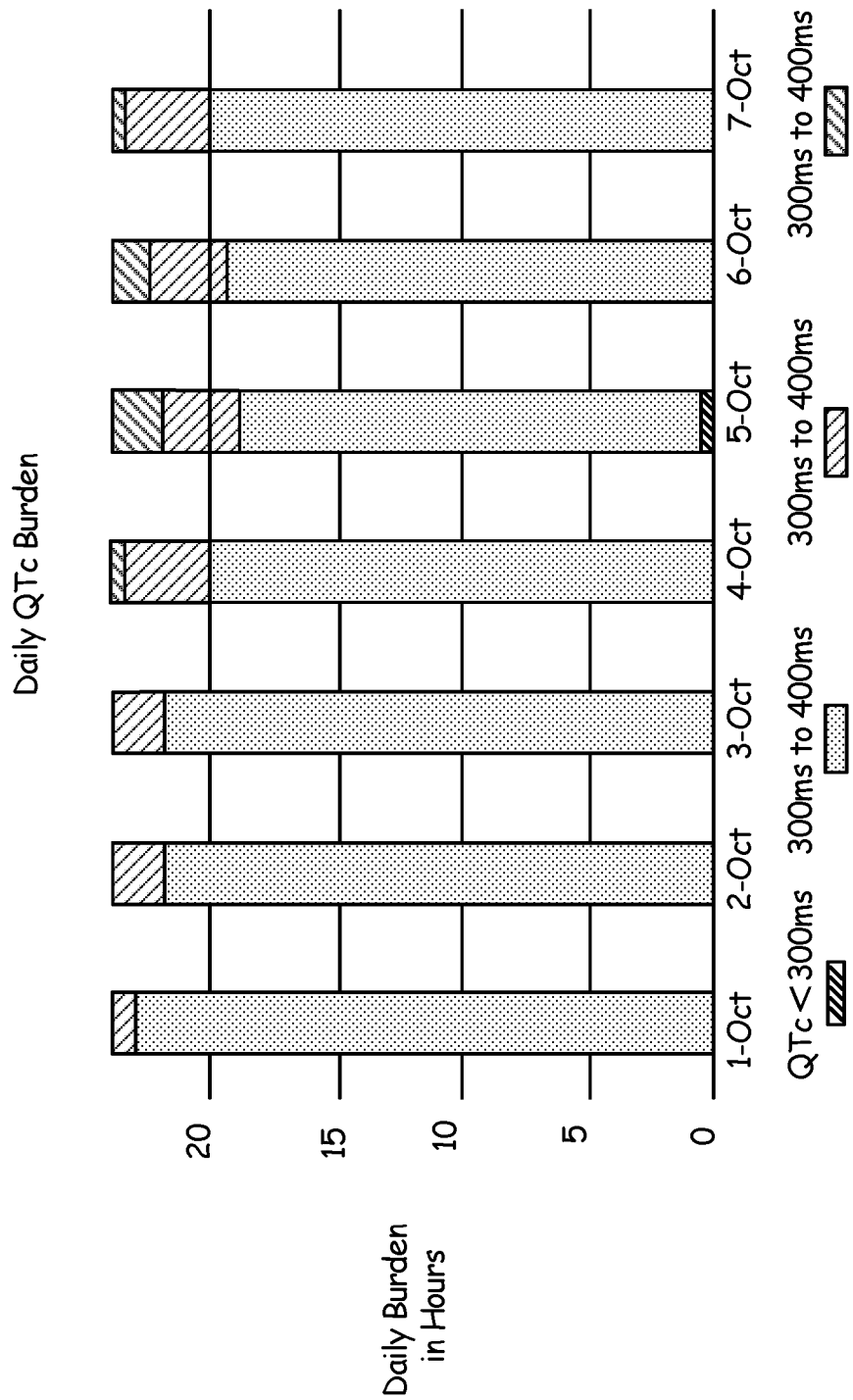
Figure 9C:
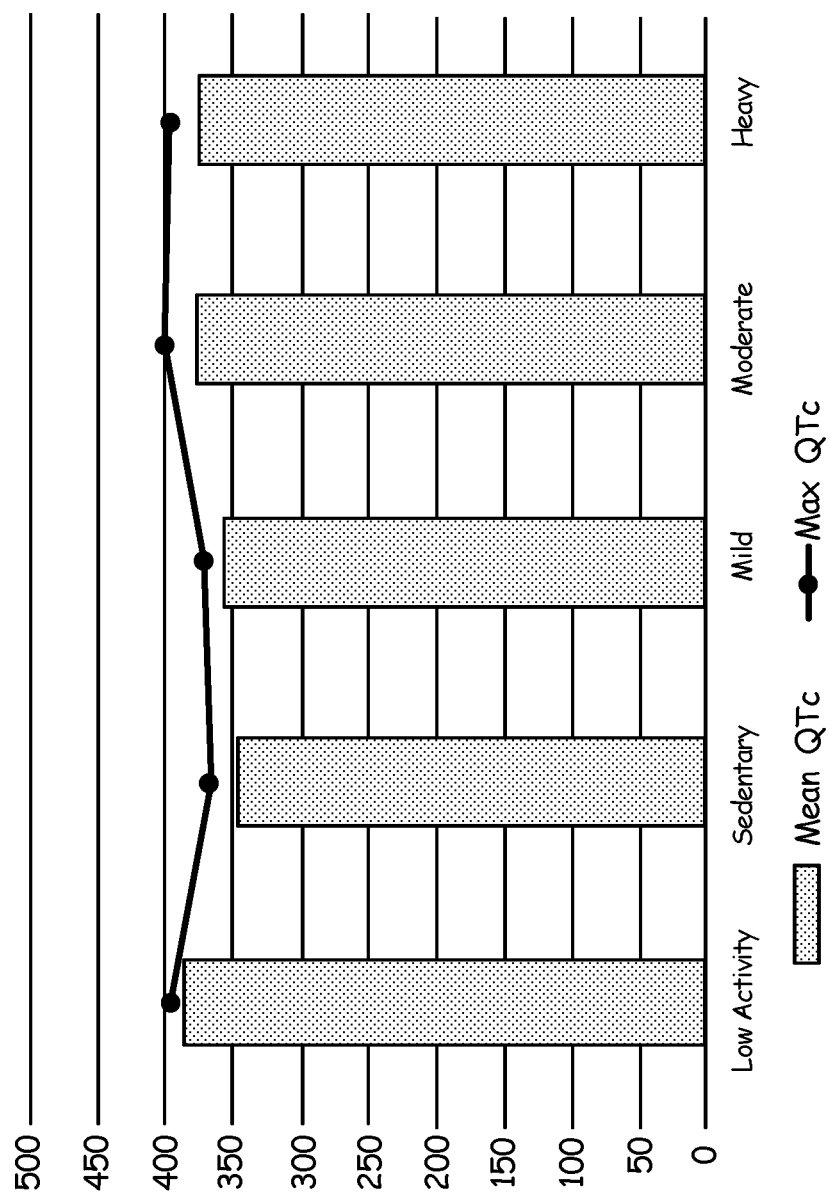

FIGS. 9A-9C are displays illustrating various methods of displaying measured QT interval data according to embodiments of the present invention. Collection and display of the information illustrated in FIGS. 9A-9C may be monitored by a caregiver or medical personnel to provide a quick overview of a patient's condition. In addition to the data illustrated in FIGS. 9A-9C, more detailed QTc data may be made available to a caregiver or medical personnel along with raw EKG signals. In addition, it should be noted that displays shown in FIGS. 9A-9C are not exhaustive of how corrected QT interval data can be displayed.

In the embodiment shown in FIG. 9A, QT interval measurements corrected as described above based on heart rate information (e.g., QTc data) is displayed versus time to allow trends in the patient's QT interval to be analyzed. The length of time may vary depending on the application from several hours to several weeks or more. In the embodiment shown in FIG. 9A, QTc data is shown for a seven day period, which measured QT data including a mean QTc value, maximum QTc value, and a minimum QTc value. The information illustrated in FIG. 9A allows a caregiver or medical personnel to quickly determine trends in the patient's QT interval.

In the embodiment shown in FIG. 9B, corrected QT intervals QTc are grouped into bins and displayed versus time. For example, the example shown in FIG. 9B consists of four bins each representing a different range of corrected QT intervals. In the embodiment shown in FIG. 9B, the first bin is defined as less than 300 milliseconds (ms), the second bin is defined as between 300 ms and 400 ms, and third bin is defined as between 400 ms and 450 ms, and the fourth bin is defined as greater than 450 ms. Each measured QT interval is placed into one of the defined bins, and the graphical display shown in FIG. 9B visually illustrates the number of measurements collected in each bin. In this way, a reviewing caregiver or medical personnel can visually review the number of QT intervals that are considered out of spec or long. For example, in the embodiment shown in FIG. 9B, on the October 5$^{th}$ date, a number of measured QT intervals are greater than 450 ms.

In the embodiment shown in FIG. 9C, corrected QT intervals are correlated with the patient's activity level. In one embodiment, activity level is determined based on heart rate information, 3D accelerometer information, activity sensor, or a combination thereof. In the embodiment shown in FIG. 9C, activity levels include low activity, sedentary, mild, moderate and heavy. As part of the measuring process, a determination is made of the patient's current activity level and corrected QT intervals measured during this time are associated with the identified activity level. In the embodiment shown in FIG. 9C, both mean corrected QT intervals and maximum corrected QT intervals are displayed. The display shown in FIG. 9C allows a caregiver or medical personnel to quickly review data and detect trends related to activity level of the patient. It should be noted, that while the QT interval will decrease in time with increasing activity (e.g., increasing heart rate), the corrected QT interval QTc corrects the measured QT interval based on heart rate, so that measurements taken during heavy activity reflect this correction of the measured QT interval.

In each of the examples shown in with respect to FIGS. 9A-9C, the goal is provide an output or display that allows a caregiver or medical personnel to quickly identify potentially problematic issues. In addition to this type of display, calculated QT intervals (both corrected and non-corrected) and measured EKG signals may be provided for review by the caregiver and/or medical personnel. In one embodiment, the displays shown in FIG. 9A-9C are used as a preliminary review of QT intervals associated with a patient, with additional information provided to a caregiver or medical personnel upon request or if a threshold is crossed with respect to the information shown in FIGS. 9A-9C.

FIGS. 10A and 10B show an exploded view and a side cross-sectional view, respectively, of adherent devices utilized to measure EKG signals according to embodiments of the present invention. The adherent device 100 may comprise an adherent patch 110 with an adhesive 116B, electrodes 112A, 112B, 112C, 112D with gels 114A, 114B, 114C, 114D, gel cover 180, temperature sensor 177, cover 162, and a printed circuit board (PCB) 120 with various circuitry for monitoring physiological sensors, communicating wirelessly with a remote center, and providing alerts when necessary. The adherent device 100 comprises at least two electrodes and in the embodiment shown in FIGS. 9A and 9B is comprised of four electrodes 112A, 112B, 112C and 112D. Adherent device 100 may comprise a maximum dimension, for example a maximum length from about 4 to 10 inches, a maximum thickness along a profile of the device from about 0.2 inches to about 0.6 inches, and a maximum width from about 2 to about 4 inches.

The adherent patch 110 comprises a first side, or a lower side 110A, that is oriented toward the skin of the patient when placed on the patient. The adherent patch 110 may also comprise a tape 110T which is a material, preferably breathable, with an adhesive 116A to adhere to patient P. Electrodes 112A, 112B, 112C and 112D are affixed to adherent patch 110. In many embodiments, at least four electrodes are attached to the patch. Gels 114A, 114B, 114C and 114D can each be positioned over electrodes 112A, 112B, 112C and 112D, respectively, to provide electrical conductivity between the electrodes and the skin of the patient. Adherent patch 100 also comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient.

In many embodiments, adherent patch 110 may comprise a layer of breathable tape 110T, for example a tricot-knit polyester fabric, to allow moisture vapor and air to circulate to and from the skin of the patient through the tape. In many embodiments, breathable tape 110T comprises a backing material, or backing 111, with an adhesive. In many embodiments, the backing is conformable and/or flexible, such that the device and/or patch do not become detached with body movement. In many embodiments, the adhesive patch may comprise from 1 to 2 pieces, for example 1 piece. In many embodiments, adherent patch 110 comprises pharmacological agents, such as at least one of beta blockers, ace inhibiters, diuretics, steroid for inflammation, antibiotic, antifungal agent, and cortisone steroid. Patch 110 may comprise many geometric shapes, for example at least one of oblong, oval, butterfly, dogbone, dumbbell, round, square with rounded corners, rectangular with rounded corners, or a polygon with rounded corners. In specific embodiments, a thickness of adherent patch 110 is within a range from about 0.001" to about 0.020", length of the patch is within a range from about 2" to about 10", and width of the patch is within a range from about 1" to about 5".

In many embodiments, the adherent device 100 comprises a temperature sensor 177 disposed over a peripheral portion of gel cover 180 to allow the temperature near the skin to be measured through the breathable tape and the gel cover. Temperature sensor 177 can be affixed to gel cover 180 such that the temperature sensor can move when the gel cover stretches and tape stretch with the skin of the patient. Temperature sensor 177 may be coupled to temperature sensor circuitry 144 through a flex connection comprising at least one of wires, shielded wires, non-shielded wires, a flex circuit, or a flex PCB. The temperature sensor can be affixed to the breathable tape, for example through a cutout in the gel cover with the temperature sensor positioned away from the gel pads. A heat flux sensor can be positioned near the temperature sensor for example to measure heat flux through to the gel cover.

The adherent device comprises electrodes 112A, 112B, 112C and 112D configured to couple to tissue through apertures in the breathable tape 110T. Electrodes 112A, 112B, 112C and 112D can be fabricated in many ways, for example printed on a flexible connector 112F, such as silver ink on polyurethane. In some embodiments, the electrodes may comprise at least one of carbon-filled ABS plastic, Ag/AgCl, silver, nickel, or electrically conductive acrylic tape. The electrodes may comprise many geometric shapes to contact the skin, for example at least one of square, circular, oblong, star shaped, polygon shaped, or round. In specific embodiments, a dimension across a width of each electrode is within a range from about 002" to about 0.050". In specific embodiments, the two inside electrodes may comprise force, or current electrodes, with a center to center spacing within a range from about 20 to about 50 mm. In specific embodiments, the two outside electrodes may comprise measurement electrodes, for example voltage electrodes, and a center-center spacing between adjacent voltage and current electrodes is within a range from about 15 mm to about 35 mm. Therefore, in many embodiments, a spacing between inner electrodes may be greater than a spacing between an inner electrode and an outer electrode.

In many embodiments, gel 114A, or gel layer, comprises a hydrogel that is positioned on electrode 112A and provides a conductive interface between skin and electrode, so as to reduce impedance between electrode/skin interface. The gel may comprise water, glycerol, and electrolytes, pharmacological agents, such as beta blockers, ace inhibiters, diuretics, steroid for inflammation, antibiotic, and antifungal agents. Gels 114A, 114B, 114C and 114D can be positioned over electrodes 112A, 112B, 112C and 112D, respectively, so as to couple electrodes to the skin of the patient. The flexible connector 112F comprising the electrodes can extend from under the gel cover to the PCB to connect to the PCB and/or components supported thereon. For example, flexible connector 112F may comprise flexible connector 122A to provide strain relief.

A gel cover 180, or gel cover layer, for example a polyurethane non-woven tape, can be positioned over patch 110 comprising the breathable tape to inhibit flow of gels 114A-114D through breathable tape 110T. Gel cover 180 may comprise at least one of a polyurethane, polyethylene, polyolefin, rayon, PVC, silicone, non-woven material, foam, or a film. Gel cover 180 may comprise an adhesive, for example an acrylate pressure sensitive adhesive, to adhere the gel cover to adherent patch 110. In many embodiments, the gel cover can regulate moisture of the gel near the electrodes so as to keeps excessive moisture, for example from a patient shower, from penetrating gels near the electrodes. A PCB layer, for example the flex PCB 120, or flex PCB layer, can be positioned over gel cover 180 with electronic components 130 connected and/or mounted to the flex PCB 120, for example mounted on flex PCB so as to comprise an electronics layer disposed on the flex PCB layer. In many embodiments, the gel cover may avoid release of excessive moisture form the gel, for example toward the electronics and/or PCB modules. In many embodiments, a thickness of gel cover is within a range from about 0.0005" to about 0.020". In many embodiments, gel cover 180 can extend outward from about 0-20 mm from an edge of gels. Gel layer 180 and breathable tape 110T comprise apertures 180A, 180B, 180C and 180D through which electrodes 112A-112D are exposed to gels 114A-114D.

In many embodiments, device 100 includes a printed circuitry, for example a PCB module that includes at least one PCB with electronics component mounted thereon. The printed circuit may comprise polyester film with silver traces printed thereon. Rigid PCB's 120A, 120B, 120C and 120D with electronic components may be mounted on the flex PCB 120. In many embodiments, the PCB module comprises two rigid PCB modules with associated components mounted therein, and the two rigid PCB modules are connected by flex circuit, for example a flex PCB. In specific embodiments, the PCB module comprises a known rigid FR4 type PCB and a flex PCB comprising known polyimide type PCB. Batteries 150 may be positioned over the flex PCB and electronic components. Batteries 150 may comprise rechargeable batteries that can be removed and/or recharged. A cover 162 may be placed over the batteries, electronic components and flex PCB. In specific embodiments, the PCB module comprises a rigid PCB with flex interconnects to allow the device to flex with patient movement. The geometry of flex PCB module may comprise many shapes, for example at least one of oblong, oval, butterfly, dogbone, dumbbell, round, square, rectangular with rounded corners, or polygon with rounded corners. In specific embodiments the geometric shape of the flex PCB module comprises at least one of dogbone or dumbbell. The PCB module may comprise a PCB layer with flex PCB 120 that can be positioned over gel cover 180 and electronic components 130 connected and/or mounted to flex PCB 120. In many embodiments, the adherent device may comprise a segmented inner component, for example the PCB, for limited flexibility.

In many embodiments, an electronics housing 160 encapsulates the electronics layer. Electronics housing 160 may comprise an encapsulant, such as a dip coating, which may comprise a waterproof material, for example silicone, epoxy, other adhesives and/or sealants. In many embodiments, the PCB encapsulant protects the PCB and/or electronic components from moisture and/or mechanical forces. The encapsulant may comprise silicone, epoxy, other adhesives and/or sealants. In some embodiments, the electronics housing may comprising metal and/or plastic housing and potted with aforementioned sealants and/or adhesives.

In many embodiments, cover 162 can encase the flex PCB, electronics, and/or adherent patch 110 so as to protect at least the electronics components and the PCB. In some embodiments, cover 162 can be adhered to adherent patch 110 with an adhesive 164 or adhesive 116B on an underside of cover 162. In many embodiments, cover 162 attaches to adherent patch 110 with adhesive 116B, and cover 162 is adhered to the PCB module with an adhesive 161 on the upper surface of the electronics housing. Cover 162 can comprise many known biocompatible cover materials, for example silicone, an outer polymer cover to provide smooth contour without limiting flexibility, a breathable fabric, or a breathable water resistant cover. In some embodiments, the breathable fabric may comprise polyester, nylon, polyamide, and/or elastane (Spandex™). Work in relation to embodiments of the present invention suggests that these coatings can be important to keep excessive moisture from the gels near the electrodes and to remove moisture from body so as to provide patient comfort.

In many embodiments, cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along the length and width of the adherent patch with the skin of the patient, and stretching along the length can increase spacing between electrodes. Stretching of the cover and adherent patch 110 can extend the time the patch is adhered to the skin as the patch can move with the skin. Electronics housing 160 can be smooth and allow breathable cover 162 to slide over electronics housing 160, such that motion and/or stretching of cover 162 is slidably coupled with housing 160. The PCB can be slidably coupled with adherent patch 110 that comprises breathable tape 110T, such that the breathable tape can stretch with the skin of the patient when the breathable tape is adhered to the skin of the patient, for example along two dimensions comprising the length and the width.

The breathable cover 162 and adherent patch 110 comprise breathable tape that can be configured to couple continuously for at least one week the at least one electrode to the skin so as to measure breathing of the patient. The breathable tape may comprise the stretchable breathable material with the adhesive and the breathable cover may comprises a stretchable breathable material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A-122D between PCB 130 and electrodes 112A-112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient.

The PCB 120 may be adhered to the adherent patch 110 comprising breathable tape 110T at a central portion, for example a single central location, such that adherent patch 110 can stretched around this central region. The central portion can be sized such that the adherence of the PCB to the breathable tape does not have a substantial effect of the modulus of the composite modulus for the fabric cover, breathable tape and gel cover, as described above. For example, the central portion adhered to the patch may be less than about 100 mm$^2$, for example with dimensions that comprise no more than about 10% of the area of patch 110, such that patch 110 can stretch with the skin of the patient. Electronics components 130, PCB 120, and electronics housing 160 are coupled together and disposed between the stretchable breathable material of adherent patch 110 and the stretchable breathable material of cover 160 so as to allow the adherent patch 110 and cover 160 to stretch together while electronics components 130, PCB 120, and electronics housing 160 do not stretch substantially, if at all. This decoupling of electronics housing 160, PCB 120 and electronic components 130 can allow the adherent patch 110 comprising breathable tape to move with the skin of the patient, such that the adherent patch can remain adhered to the skin for an extended time of at least one week.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of PCB 120 and electronic components 130, as indicated by arrows 186. PCB 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers. Gap 169 extends from adherent patch 110 to the electronics module and/or PCB a distance within a range from about 0.25 mm to about 4 mm.

In many embodiments, the adherent device comprises a patch component and at least one electronics module. The patch component may comprise adherent patch 110 comprising the breathable tape with adhesive coating 116A, at least one electrode, for example electrode 112A and gel 114A. The at least one electronics module can be separable from the patch component. In many embodiments, the at least one electronics module comprises the flex PCB 120, electronic components 130, electronics housing 160 and cover 162, such that the flex PCB, electronic components, electronics housing and cover are reusable and/or removable for recharging and data transfer, for example as described above. In specific embodiments, the electronic module can be adhered to the patch component with a releasable connection, for example with Velcro™, a known hook and loop connection, and/or snap directly to the electrodes. Monitoring with multiple adherent patches for an extended period is described in U.S. Pub. No. 2009-0076345-A1, published on Mar. 19, 2009, the full disclosure of which has been previously incorporated herein by reference, and which adherent patches and methods are suitable for combination in accordance with embodiments described herein.

The adherent device 100, shown in FIG. 10A, may comprise an X-axis, Y-axis and Z-axis for use in determining the orientation of the adherent device 100 and/or the patient P. Electric components 130 may comprise a 3D accelerometer. As the accelerometer of adherent device 100 can be sensitive to gravity, inclination of the patch relative to an axis of the patient can be measured, for example when the patient stands. Vectors from a 3D accelerometer can be used to determine the orientation of a measurement axis of the patch adhered on the patient and can be used to determine the angle of the patient, for example whether the patient is laying horizontally or standing upright, when measured relative to the X-axis, Y-axis and/or X-axis of adherent device 100.

FIG. 10B shows a PCB and electronic components over adherent patch 110. In some embodiments, PCB 120, for example a flex PCB, may be connected to electrodes 112A, 112B, 112C and 112D of FIG. 10B with connectors 122A, 122B, 122C and 122D, respectively, and may include traces 123A, 123B, 123C and 123D that extend to connectors 122A, 122B, 122C and 122D. In some embodiments, connectors 122A-122D may comprise insulated wires and/or a film with conductive ink that provide strain relief between the PCB and the electrodes.

Electronic components 130 comprise components to take physiologic measurements, transmit data to intermediate device 14 (shown in FIG. 1) and receive commands and/or timing signals from intermediate device 14. In many embodiments, electronics components 130 may comprise known low power circuitry, for example complementary metal oxide semiconductor (CMOS) circuitry components. Electronics components 130 comprise a temperature sensor, an activity sensor and activity circuitry 134, impedance circuitry 136 and electrocardiogram circuitry, for example ECG circuitry 138. In some embodiments, electronic circuitry 130 may comprise a microphone and microphone circuitry 142 to detect an audio signal, such as heart or respiratory sound, from within the patient.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer can comprise a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example hydration data. In addition, impedance circuitry 136 can generate both hydration data and respiration data. These physiological parameters can be utilized in conjunction with the measured EKG signals to determine whether or not segments of beats should be analyzed for conditions such as long QT syndrome, and may be used in conjunction with measured QT intervals to diagnose underlying conditions.

In many embodiments, impedance circuitry 136 is electrically connected to electrodes 112A, 112B, 112C and 112D of FIG. 10A in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112D may comprise sense electrodes. The voltage measured by the sense electrodes can be used to measure the impedance of the patient and determine the respiration rate and/or hydration of the patient. In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In many embodiments, the ECG circuitry may measure the ECG signal from electrodes 112A and 112D when current is not passed through electrodes 112A and 112D.

Electronic circuitry 130 may comprise a processor 146 that can be configured to control a collection, analysis and/or transmission of data from the impedance circuitry electrocardiogram circuitry and the accelerometer. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 146 may comprise the frequency generator and real time clock. In many embodiments, device 100 comprises a distributed processor system, for example with multiple processors on device 100.

In many embodiments, electronics components 130 comprise wireless communications circuitry 132 to communicate with intermediate device 14 (shown in FIG. 1). PCB 120 may comprise an antenna to facilitate wireless communication. The antenna may be integral with PCB 120 or may be separately coupled thereto. The wireless communication circuitry can be coupled to the impedance circuitry, the electrocardiogram circuitry and the accelerometer to transmit to a remote center with a communication protocol at least one of the hydration signal, the electrocardiogram (EKG) signal or the activity/inclination signal. In specific embodiments, wireless communication circuitry 132 is configured to transmit the hydration signal, the electrocardiogram signal and the inclination signal to the remote monitoring system 16 (shown in FIG. 1) either directly or through intermediate device 14 (also shown in FIG. 1). The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

In many embodiments, the electrodes are connected to the PCB with a flex connection, for example trace 123A, 123B, 123C and 123D of flex PCB 120, so as to provide strain relief between the electrodes 112A, 112B, 112C and 112D and the PCB. In such embodiments, motion of the electrodes relative to the electronics modules, for example rigid PCB's 120A, 120B, 120C and 120D with the electronic components mounted thereon, does not compromise integrity of the electrode/hydrogel/skin contact. In many embodiments, the flex connection comprises at least one of wires, shielded wires, non-shielded wires, a flex circuit, or a flex PCB. In specific embodiments, the flex connection may comprise insulated, non-shielded wires with loops to allow independent motion of the PCB module relative to the electrodes.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A monitoring system for measuring QT intervals, the monitoring system comprising:
a monitoring device adhered to a patient at a location and configured to monitor an electrocardiogram (EKG) signal associated with the patient; and
a QT interval measurement module configured to:
receive the EKG signal from the monitoring device;
identify QRS complex attributes and heart rate attributes for each beat within the received EKG signal, wherein the QRS complex attributes include a peak of a QRS complex (iRpk) and a QRS onset (iRon);
generate a T-wave offset estimate (iToff_estimate) based at least in part on the identified heart rate attributes;
identify a T-wave offset detection window based on the identified peak of the QRS complex (iRpk) and the generated T-wave offset estimate (iToff_estimate);
locate a T-wave offset (iToff) within the identified T-wave offset detection window based on one or more detected maximums or minimums within the T-wave offset detection window; and
measure a QT interval based on the identified QRS onset (iRon) and the located T-wave offset (iToff).

2. The monitoring system of claim 1, wherein the QT interval measurement module is further configured to generate an alert in response to detecting a long QT interval.

3. The monitoring system of claim 2, wherein the QT interval measurement module is further configured to provide the generated alert and the received EKG signal to a remote monitoring center.

4. The monitoring system of claim 1,
wherein the QT interval measurement module is further configured to:
identify beats within the received EKG signal as noisy or non-noisy; and
identify a beat segment as non-noisy in response to identifying a consecutive number of beats as non-noisy,
wherein to measure the QT interval, the QT interval measurement module is configured to select only non-noisy beat segments.

5. The monitoring system of claim 1, wherein the QT interval measurement module is further configured to select a beat segment to measure the QT interval based on one or more of a time of day, an activity level of the patient, an orientation of the patient, or a heart rate of the patient.

6. The monitoring system of claim 1, wherein the QT interval measurement module is further configured to discards beats in which the QT interval measurement module cannot discern at least one of the QRS onset (iRon) or the T-wave offset (iToff) within the EKG signal even if the beat is non-noisy.

7. The monitoring system of claim 1, wherein the T-wave offset detection window starts from the generated T-wave offset estimate (iToff_estimate) and extends by a threshold value.

8. The monitoring system of claim 1, wherein to generate the T-wave offset estimate (iToff_estimate) based at least in part on the identified heart rate attributes, the QT interval measurement module is configured to use the identified heart rate attributes and a look-up table to estimate the T-wave offset detection window.

9. The monitoring system of claim 1, wherein the QT interval measurement module is located in an intermediate device that comprises:
   a processor configured to execute for executing instructions stored in a computer readable medium; and
   an antenna configured to receive the EKG signal from the monitoring device.

10. A method for measuring QT intervals, the method comprising:
   receiving an electrocardiogram (EKG) signal associated with a patient;
   identifying QRS complex attributes and heart rate attributes for each beat within the received EKG signal, wherein the QRS complex attributes include a peak of a QRS complex (iRpk) and a QRS onset (iRon);
   generating a T-wave offset estimate (iToff_estimate) based at least in part on the identified heart rate attributes;
   identifying a T-wave offset detection window based on the identified peak of the QRS complex (iRpk) and the generated T-wave offset estimate (iToff_estimate);
   locating a T-wave offset (iToff) within the identified T-wave offset detection window based on one or more detected maximums or minimums within the T-wave offset detection window; and
   measuring a QT interval based on the identified QRS onset (iRon) and the located T-wave offset (iToff).

11. The method of claim 10, further comprising:
   identifying beats within the received EKG signal as noisy or non-noisy; and
   setting beat-wise noise flags with respect to those beats identified as noisy.

12. The method of claim 11, further comprising identifying a qualified beat segment within the EKG signal, wherein the qualified beat segment comprises at least a threshold number of consecutive non-noisy beats.

13. The method of claim 12, wherein measuring the QT interval comprises measuring the QT measured with respect to only qualified beat segments.

14. The method of claim 10, further comprising setting a long QT syndrome flag in response to determining that the measured QT interval exceeds a threshold value.

15. The method of claim 10, further comprising:
   storing the QT interval; and
   using the QT interval as a benchmark for comparison to subsequently measured QT intervals.

16. A device comprising:
   an antenna configured to receive an electrocardiogram (EKG) signal associated with the patient;
   a memory operably coupled to a processor; and
   the processor, wherein the processor is configured to:
      identify QRS complex attributes and heart rate attributes for each beat within the received EKG signal, wherein the QRS complex attributes include a peak of a QRS complex (iRpk) and a QRS onset (iRon);
      generate a T-wave offset estimate (iToff_estimate) based at least in part on the identified heart rate attributes;
      identify a T-wave offset detection window based on the identified peak of the QRS complex (iRpk) and the generated T-wave offset estimate (iToff_estimate);
      locate a T-wave offset (iToff) within the identified T-wave offset detection window based on one or more detected maximums or minimums within the T-wave offset detection window;
      measure a QT interval based on the identified QRS onset (iRon) and the located T-wave offset (iToff); and
      output an indication of the measured QT interval to a remote monitoring center.

17. The device of claim 16, wherein the processor is further configured to:
   determine that the measured QT interval is a long QT interval; and
   generate, in response to determining that the measured QT interval is a long QT interval, an alert.

18. The device of claim 17, wherein the processor is further configured to output, to the remote monitoring center, the alert and the received EKG signal.

19. The device of claim 16,
   wherein the processor is further configured to:
      identify beats within the received EKG signal as noisy or non-noisy; and
      identify a beat segment as non-noisy in response to identifying a consecutive number of beats as non-noisy,
   wherein to measure the QT interval, the processor is configured to select only non-noisy beat segments.

20. The device of claim 16, wherein the T-wave offset detection window starts from the generated T-wave offset estimate (iToff_estimate) and extends by a threshold value.

* * * * *